(12) United States Patent
Girardet et al.

(10) Patent No.: US 8,481,581 B2
(45) Date of Patent: *Jul. 9, 2013

(54) S-TRIAZOLYL α-MERCAPTOACETANILIDES AS INHIBITORS OF HIV REVERSE TRANSCRIPTASE

(75) Inventors: Jean-Luc Girardet, San Diego, CA (US); Yung-Hyo Koh, Irvine, CA (US); Martha De La Rosa, Durham, NC (US); Esmir Gunic, San Diego, CA (US); Zhi Hong, Chapel Hill, NC (US); Stanley Lang, Concord Twp, OH (US); Hong-Woo Kim, Cambridge, MA (US)

(73) Assignee: Ardea Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,443

(22) Filed: Jul. 18, 2012

(65) Prior Publication Data

US 2012/0283301 A1 Nov. 8, 2012

Related U.S. Application Data

(60) Continuation of application No. 13/174,538, filed on Jun. 30, 2011, now Pat. No. 8,252,828, which is a continuation of application No. 13/081,398, filed on Apr. 6, 2011, which is a division of application No. 11/661,079, filed as application No. PCT/US2005/030259 on Aug. 25, 2005, now Pat. No. 7,947,721.

(60) Provisional application No. 60/686,351, filed on May 31, 2005, provisional application No. 60/604,219, filed on Aug. 25, 2004, provisional application No. 60/604,220, filed on Aug. 25, 2004.

(51) Int. Cl.
*A61K 31/4196* (2006.01)
*C07D 249/08* (2006.01)

(52) U.S. Cl.
USPC ............ 514/384; 548/262.2; 548/263.8; 514/383

(58) Field of Classification Search
USPC .......... 548/262.2, 263.2, 263.8; 514/383, 514/384
See application file for complete search history.

(56) References Cited

U.S. PATENT DOCUMENTS

| | | | |
|---|---|---|---|
| 5,939,462 A | 8/1999 | Connell et al. | |
| 6,197,779 B1 | 3/2001 | Andries et al. | |
| 6,245,817 B1 | 6/2001 | Connell et al. | |
| 6,414,147 B1 | 7/2002 | Currie et al. | |
| 7,435,752 B2 * | 10/2008 | Girardet et al. | 514/384 |
| 7,642,277 B2 | 1/2010 | Simoneau et al. | |
| 7,683,087 B2 * | 3/2010 | Girardet et al. | 514/384 |
| 7,947,721 B2 * | 5/2011 | Girardet et al. | 514/384 |
| 8,106,205 B2 * | 1/2012 | Girardet et al. | 546/167 |
| 8,252,828 B2 * | 8/2012 | Girardet et al. | 514/384 |
| 2002/0026186 A1 | 2/2002 | Woloszko et al. | |
| 2003/0027433 A1 | 2/2003 | Faur et al. | |
| 2005/0054639 A1 | 3/2005 | Simoneau | |
| 2006/0135556 A1 | 6/2006 | Girardet et al. | |
| 2006/0270725 A1 | 11/2006 | Girardet et al. | |
| 2008/0176850 A1 | 7/2008 | Girardet | |
| 2008/0249131 A1 | 10/2008 | Girardet et al. | |
| 2008/0319201 A1 | 12/2008 | Girardet et al. | |
| 2009/0197825 A1 | 8/2009 | Quart et al. | |
| 2010/0069645 A1 | 3/2010 | Girardet | |
| 2010/0081827 A1 | 4/2010 | Girardet | |
| 2010/0137590 A1 | 6/2010 | Girardet | |
| 2011/0064994 A1 | 3/2011 | Lin | |

FOREIGN PATENT DOCUMENTS

| | | |
|---|---|---|
| CA | 1050531 | 3/1979 |
| EP | 1545483 | 6/2005 |
| EP | 1789039 | 5/2007 |
| EP | 2135608 | 12/2009 |
| JP | 7215940 | 8/1995 |
| WO | WO-00-27850 | 5/2000 |
| WO | WO-02-070470 | 9/2002 |
| WO | WO-03-016306 | 2/2003 |
| WO | WO-03-097047 | 11/2003 |
| WO | WO-2004-030611 | 4/2004 |
| WO | WO-2004-050643 | 6/2004 |
| WO | WO-2004-069812 | 8/2004 |

(Continued)

OTHER PUBLICATIONS

U.S. Appl. No. 13/174,538, filed Jun. 30, 2011, Girardet.
Ainsworth, C. 1,2,4-Triazole. Org. Syn., Coll. 1973; vol. V: 1070. (4 pages).
Badger, et al. Azaindoles. III. The synthesis of pyrazolo[3,4-b]pyridines and pyrazolo-[3,4-d]pyrimidines. Aust. J. Chem. 1965; 18(8): 1267-71.
Berge, et al. Pharmaceutical salts. J. Pharm. Sci. 1977; 66(1): 1-19.
Bontems, et al. Guanosine analogues: Synthesis of nucleosides of certain 3-substituted 6-aminopyrazolo[3,4-d]pyrimidin-4(5H)-ones as potential immunotherapeutic agents. J. Med. Chem. 1990; 33(8): 2174-8.

(Continued)

*Primary Examiner* — Golam M M Shameem
(74) *Attorney, Agent, or Firm* — Wilson, Sonsini, Goodrich & Rosati

(57) ABSTRACT

A series of S-triazolyl α-mercaptoacetanilides having general structure (1) are provided, where Q is $CO_2H$, $CONR_2$, $SO_3H$, or $SO_2NR_2$. The compounds inhibit several variants of the reverse transcriptase of HIV, and are useful in the treatment of HIV infections.

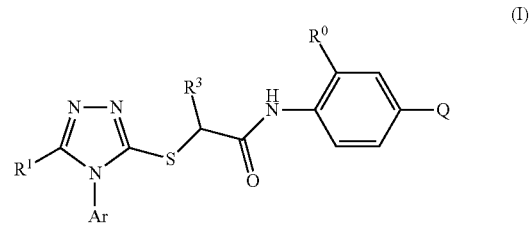

(I)

8 Claims, No Drawings

FOREIGN PATENT DOCUMENTS

| | | |
|---|---|---|
| WO | WO-2005-028479 | 3/2005 |
| WO | WO-2007-050087 | 5/2007 |
| WO | WO-2010-048592 | 4/2010 |
| WO | WO-2010-048593 | 4/2010 |

OTHER PUBLICATIONS

Connor, et al. Characterization of the functional properties of env genes from long-term survivors of human immunodeficiency virus type 1 infection. J. Virol. 1996; 70(8): 5306-11.
EP 03786506 Supplementary Search Report dated Feb. 2, 2009.
EP 05790722 Search Opinion dated Jul. 3, 2009.
EP 05790722 Search Report dated Jun. 26, 2009.
EP 09170772 Search Opinion dated Nov. 9, 2009.
EP 09170772 Search Report dated Oct. 14, 2009.
EP 11177941 Search Report dated Dec. 7, 2011.
Harrington, et al. Direct detection of infectious HIV-1 in blood using a centrifugation-indicator cell assay. J. Viral. Methods. 2000; 88(1): 111-5.
Ibata, et al. Formation and reaction of oxazoles: Synthesis of N-substituted 2-(aminomethyl)oxazoles. Bull. Chem. Soc. Jpn. 1989; 62: 618-20.
Ibata, et al. The acid catalyzed decomposition of diazo compounds. I. Synthesis of oxazoles in the BF3 catalyzed reaction of diazo carbonyl compounds with nitriles. Bull. Chem. Soc. Jpn. 1979; 52: 3597-600.
Larsen, et al. Prodrug forms for the sulfonamide group. I: Evaluation of N-acyl derivatives, N-sulfonylamidines, N-sulfonylfilimines and sulfonylureas as possible prodrug derivatives. Int. J. Pharm. 1987; 37(1-2): 87-95.
Lewis, et al. Pyrazolopyrimidine nucleosides. 13. Synthesis of the novel C-nucleoside 5-amino-3-(β-D-ribofuranosyl)pyrazolo[4,3-d]pyrimidin-7-one, a guanosine analogue related to the nucleoside antibiotic formycin B. J. Am. Chem. Soc. 1988; 104: 1073-7.
Liu, et al. An improved synthesis of 9-deazaguanine. Synthetic Communications. 2002; 32(24): 3797-802, (edited by Klaus Kielich).
Lopes, et al. Acyloxymethyl as a drug protecting group. Part 6: N-acyloxymethyl- and N-[(aminocarbonyloxy)methyl]sulfonamides as prodrugs of agents containing a secondary sulfonamide group. Bioorg. Med. Chem. 2000; 8(4): 707-16.
Ludovici, et al. Evolution of anti-HIV candidates. Part 3: Diarylpyrimidine (DAPY) analogues. Bioorg. Med. Chem. Lett. 2001; 11(17): 2235-9.
Modi et al., "Synthesis of S-(4-aryl-4H-1,2,4-triazol-3y1)2-mercaptomethyl benuimidazoles," J. Indian Chem. Soc. 54:741-742 (1977).
Modi et al., "Synthesis of substituted 1,2 arylhydrazones of 4-aryl-4H-1,2,4-triazolyl-3-thioacetic acid hydrazides," J. Indian Chem. Soc. 54:1087-1089 (1977).
Olesen, P. The use of bioisosteric groups in lead optimization. Current Opinion in Drug Discovery & Development. 2001; 4: 471-78.
Patani, et al. Bioisosterism: A rational approach in drug design. Chem. Rev. 1996; 96(8): 3147-76.
PCT/US03/27433 IPRP dated Jun. 14, 2004.
PCT/US03/27433 Search Report dated Mar. 26, 2004.
PCT/US05/30259 IPRP dated Feb. 28, 2007.
PCT/US05/30259 Search Report dated May 30, 2006.
PCT/US05/39294 IPRP dated Apr. 29, 2008.
PCT/US05/39294 Search Report dated Jun. 16, 2006.
PCT/US09/61969 Search Report dated Feb. 4, 2010.
PCT/US09/61970 Search Report dated Feb. 4, 2010.
Platt, et al. Effects of CCR5 and CD4 cell surface concentrations on infections by macrophagetropic isolates of human immunodeficiency virus type J. J. Virol. 1998; 72(4): 2855-64.
Popik, et al. Human immunodeficiency virus type 1 uses lipid raft-colocalized CD4 and chemokine receptors for productive entry into CD4(+) T cells. J. Virol. 2002; 76(10): 4709-22.
Poste, et al. Lipid Vesicles as Carriers for Introducing Biologically Active materials into Cells. Methods Cell Biol. 1976;14: 33-71.
Roos, et al. LuSIV cells: A reporter cell line for the detection and quantitation of a single cycle of HIV and SIV replication. Virology. 2000; 273(2): 307-15.
Scott, et al. A new route to the imidazole-2-thiones from 2-thiohydantoins. Implications in the study of ergothioneine. Biochem J. 1968; 109(2):209-15.
Seela, et al. Synthesis of 2'-deoxyribofuranosides of 8-aza-7-deazaguanine and related pyrazolo[3,4-d]pyrimidines. Helvitica Chimica Acta. 1986; 69(7): 1602-13.
Seela, et al. The high-anti conformation of 7-halogenated 8-aza-7-deaza-2'-deoxy-guanosines: A study of the influence of modified bases on the sugar structure of nucleosides. Helvitica Chimica Acta. 1999; 82(1): 105-24.
Taylor, et al. Synthesis of pyrazolo[3,4-d]pyrimidine analogues of the potent antitumor agent N-{4-[2-amino-4(3H)-oxo-7H-pyrrolo[2,3-d]pyrimidin-5-yl)ethyl]benzoyl}-L-glutamic acid (LY231514). Tetrahedron. 1992; 48(37): 8089-100.
Youssif, et al. A Facile One-pot Synthesis of Fused 2-Thiouracils: Dipyrimidinopyridine, Pyrazolopyrimidine and Pyridazinopyrimidines. Bull. Kor. Chem. Soc. 2003; 24: 1429-32.

* cited by examiner

S-TRIAZOLYL α-MERCAPTOACETANILIDES AS INHIBITORS OF HIV REVERSE TRANSCRIPTASE

RELATED APPLICATIONS

This application is a continuation of U.S. application Ser. No. 13/174,538, filed Jun. 30, 2011, and U.S. application Ser. No. 13/081,398, filed Apr. 6, 2011, all three of which are divisional applications of U.S. application Ser. No. 11/661,079, filed Mar. 20, 2008, and patented as U.S. Pat. No. 7,947,721 on May 24, 2011, which is the national phase entry of international application PCT/US2005/030259, filed Aug. 25, 2005, which claims priority of U.S. provisional applications 60/604,219, filed Aug. 25, 2004, 60/604,220, filed Aug. 25, 2004, and 60/686,351 filed May 31, 2005, and is related to U.S. application Ser. No. 12/618,604, filed Nov. 13, 2009, now abandoned, and U.S. application Ser. No. 12/633,638 filed Dec. 8, 2009, and patented as U.S. Pat. No. 8,003,681 on Aug. 23, 2011, the contents of each of which are incorporated herein by reference in their entirety.

FIELD OF THE INVENTION

The field of the invention is enzyme inhibitors and the use of enzyme inhibitors for treatment of disease. More particularly, the invention deals with the in vitro and in vivo inhibition of HIV reverse transcriptase as a method of treating HIV infection.

BACKGROUND OF THE INVENTION

Numerous treatments for HIV are known in the art, and among other pharmaceutically active compounds, reverse transcriptase inhibitors have provided significant therapeutic effect to many HIV infected patients. For example, lamivudine (3TC) or zidovudine (AZT) are relatively well tolerated antiretroviral drugs. However, numerous viral strains have recently emerged with marked resistance against these compounds. To overcome resistance to at least some degree, new nucleoside-type inhibitors may be administered (alone or in combination with other nucleoside-type inhibitors), and exemplary alternative drugs include stavudine (d4T), didanosine (ddI), Combivir™ (brand for a combination of lamivudine and zidovudine), and Trizivir™ (brand for a combination of 3TC, AZT, and abacavir).

Unfortunately, development of resistance to one nucleoside-type inhibitor is often accompanied by the development of a degree of resistance to another nucleoside-type inhibitor, frequently necessitating a switch to a different class of drug. In such cases, a patient may receive a protease inhibitor (e.g., saquinavir, indinavir, nelfinavir, etc.), typically in combination with other anti retroviral agents. However, the relatively complex administration regimen of such combinations often proves an organizational and financial challenge to many patients, and compliance is frequently less than desirable.

More recently, HIV treatment has focused on combination therapies that involve the administration of nucleoside reverse transcriptase inhibitors with protease inhibitors and with non-nucleoside reverse transcriptase inhibitors, and triple combinations of nucleoside reverse transcriptase inhibitors, non-nucleoside reverse transcriptase inhibitors and protease inhibitors. Unfortunately, combination therapies of protease inhibitors with nucleoside reverse transcriptase inhibitors are often poorly tolerated and frequently lead to premature termination of the therapy. Therefore, most current combination treatments include a combination of nucleoside reverse transcriptase inhibitors and non-nucleoside reverse transcriptase inhibitors.

Non-nucleoside-type inhibitors (e.g., nevirapine, delavirdine, and efavirenz) are a structurally inhomogeneous group of compounds that are thought to bind in a non-nucleoside pocket of the reverse transcriptases. They significantly increase antiviral efficacy when co-administered with nucleoside-type inhibitors. While the non-nucleoside-type inhibitors seem to provide a promising new class of antiviral drugs, several disadvantages still remain. The cost of currently-known non-nucleoside-type inhibitors is relatively high, and a single mutation in the viral reverse transcriptases can induce a cross resistance against a wide class of non-nucleoside reverse transcriptase inhibitors. Therefore, there is an urgent need to provide new non-nucleoside reverse transcriptase inhibitors that have potent antiviral effects, particularly against HIV mutant strains that exhibit resistance against currently-known non-nucleoside reverse transcriptase inhibitors.

The HIV virus has a relatively high frequency of mutation, which often leads to drug resistance to current treatments. Studies have been carried out to identify the mutation spectrum in the RT proteins of viruses isolated from patients who had failed therapies involving at least one NNRTI, and the results showed that the mutant K103N was the most predominant for patients taking efavirenz, while Y181C was predominant for patients taking nevirapine. Other single mutations included K101E, G190S/A/E and Y188L/C. Some of the most prevalent double mutations in patients failing efavirenz include K103N-P225H, K103N-V108I, K103N-K101Q, K103N-L100I, K103N-F227L, V106I-Y188L, K103N-Y188L and K103N-G190A. There is a need to provide new compositions and methods for the inhibition of these and other mutant reverse transcriptases.

The present application is related to work previously disclosed in commonly owned applications PCT/US02/26186, filed Aug. 23, 2002, unpublished, and PCT/US03/27433, filed Aug. 22, 2003, which was published as WO 2004/030611 on Apr. 15, 2004. U.S. Pat. No. 5,939,462 to Connell et al. discloses a large number of substituted heterocycles, useful as NPY5 receptor antagonists, some of which are S-triazolyl mercaptoacetanilides similar to general structure 1 below. Simoneau et al., in international patent publication WO 2004/050643, disclose tetrazoles and a few triazoles having structures similar to those of the present invention, having reverse transcriptase inhibitory activity.

BRIEF DESCRIPTION

The inventors have discovered that the reverse transcriptase (RT) of HIV may be inhibited by a select class of S-triazolyl α-mercaptoacetanilides represented by general structure 1. Surprisingly, some of these compounds were able to inhibit various mutated RTs, including K103N, Y181C and Y188L.

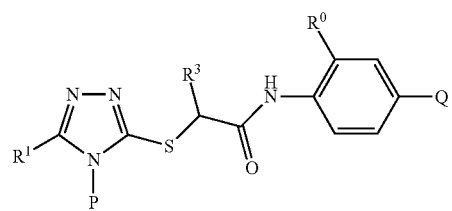

In formula 1, $R^1$ is halogen, lower alkyl, lower alkenyl, or lower alkynyl, wherein the lower alkyl, lower alkenyl, or lower alkynyl groups may optionally be substituted, preferably with one or more halogens. $R^3$ is H or methyl, and the substituent $R^0$ is H, halogen, $CF_3$, lower alkoxy, or lower alkylthio. Q is $CO_2H$, $SO_3H$, CONR'R", or $SO_2NR'R"$, wherein R' and R" are independently H, lower alkyl, or lower alkyl substituted with one or more OR, $CO_2R$, NHR, $NR_2$, or $CF_3$ groups wherein R is H or lower alkyl, or R' and R" together with the nitrogen atom to which they are attached form a 4-, 5-, or 6-membered heterocyclic ring. P is an aromatic or heteroaromatic ring having substituents as described in more detail below.

Accordingly, the present invention provides compounds that inhibit HIV reverse transcriptase in vitro and in vivo. The invention also provides pharmaceutical compositions comprising one or more of the compounds of the invention, the use of compounds of the invention for the preparation of pharmaceutical compositions for treatment of HIV, and methods of treatment of a patient infected with HIV by administration of a therapeutically effective amount of one or more of the compounds of the invention or a pharmaceutically acceptable salt thereof.

DETAILED DESCRIPTION

The term "alkyl" as used herein refers to a cyclic, branched, or straight hydrocarbon radical in which all of the carbon-carbon bonds are single bonds, and the term "lower alkyl" refers to alkyl groups of one to ten carbon atoms. The term "cycloalkyl" as used herein refers to a cyclic or polycyclic alkyl group containing 3 to 15 carbons. A cycloalkyl group may comprise multiple condensed rings in which one of the distal rings may be aromatic (e.g., indan-2-yl, tetrahydronaphth-1-yl, etc.)

Similarly, the term "alkenyl" as used herein refers to a cyclic, branched, or straight hydrocarbon radical in which one or more of the carbon-carbon bonds is a double bond, and the term "lower alkenyl" refers to alkenyl groups of one to ten carbon atoms. The term "cycloalkenyl" as used herein refers to a cyclic or polycyclic alkyl group containing 3 to 15 carbons, in which one or more of the carbon-carbon bonds is a double bond. A cycloalkenyl group may comprise multiple condensed rings in which one of the distal rings may be aromatic (e.g., inden-2-yl, 1,2-dihydronaphth-1-yl, etc.)

Likewise, the term "alkynyl" as used herein refers to an alkyl or alkenyl group, as defined above, in which at least one carbon-carbon bond has been replaced by a triple bond. The term "lower alkynyl" thus includes alkynyl groups with one to ten carbon atoms.

As used herein, the term "alkoxy" refers to an —OR group, wherein R is lower alkyl, lower alkenyl, lower alkynyl, aryl-lower alkyl, heteroaryl-lower alkyl, or heterocyclo-lower alkyl. Similarly, the term "aryloxy" refers to an —OAr group, wherein Ar is an aryl or heteroaryl group.

The terms "aryl" and "Ar" are used interchangeably herein, and refer to a monocyclic or polycyclic hydrocarbon group of 6 to 14 carbons, having at least one aromatic ring which provides the point of attachment of the group. Polycyclic aryl groups may have isolated rings (e.g. biphenyl) or condensed rings in which at least one ring is aromatic, (e.g., 1,2,3,4-tetrahydronaphth-6-yl, naphthyl, anthryl, or phenanthryl).

The terms "heterocycle" or "heterocyclic ring" are used interchangeably herein and refer to a saturated, partially unsaturated, or aromatic cycloalkyl or aryl group, having a single ring (e.g., morpholino, pyridyl or furyl) or multiple condensed rings (e.g., naphthyridyl, quinoxalinyl, quinolinyl, or indolizinyl) in which at least one carbon atom in a ring has been replaced by a heteroatom. The term "heteroatom" as used herein refers to an atom other than carbon (typically S, O, P or N). The terms "heteroaryl" and "heteroaromatic" refer to heterocycles in which at least one heterocyclic ring is aromatic.

Still further, the term "optionally substituted" as used herein means that one or more hydrogen atoms that are covalently bound to a group or substituent as defined above, or a free electron pair on a nitrogen or phosphorous atom, may be replaced by a covalently-bound non-hydrogen substituent selected from the group consisting of R, Ar, aryl-lower alkyl, OH, SH, OR, SR, OAr, SAr, $S(=O)R$, $S(=O)Ar$, $SO_2R$, $SO_2Ar$, halogen, $CF_3$, $OCF_3$, $SCF_3$, $NH_2$, NHR, $NR_2$, $NR_3+$, NHCOR, NHCOAr, $NHS(=O)R$, $NHS(=O)Ar$, $NHSO_2R$, $NHSO_2Ar$, $NO_2$, CN, $CO_2R$, $CONH_2$, CONHR, $CONR_2$, $C(=O)R$, heteroaryl, and heteroaryl-lower alkyl. In the above substituents, R is lower alkyl, lower alkenyl, lower alkynyl, aryl-lower alkyl, heteroaryl-lower alkyl, or heterocyclyl-lower alkyl.

The term "prodrug" as used herein refers to a modification of a compound of the invention, wherein the modified compound exhibits less pharmacological activity (as compared to the unmodified compound) and wherein the modified compound is converted back into the unmodified form in vivo, preferably within a target cell (e.g., a T-cell or hepatocyte) or a target organ (e.g., lymph node or spleen). Conversion of a compound of the invention into a prodrug form may be useful where the active drug is too toxic for safe systemic administration, where the unmodified compound is poorly absorbed from the digestive tract, or where the body tends to break down the unmodified compound before it reaches its target.

The term "inhibiting a reverse transcriptase" refers to a direct or indirect reduction in the formation of DNA from a template RNA or DNA by a reverse transcriptase. Direct inhibition includes suicide, competitive and non-competitive inhibition, allosteric inhibition, or binding of an inhibitor in a non-nucleoside pocket. Examples of indirect inhibition include depletion of nucleosides for DNA synthesis, induction or contribution to conformational changes, etc.

As used herein, the term "reducing viral propagation" means that the titer of a virus in a sample is lowered. The reduction may be effected in a variety of manners, including partial or total inhibition of viral replication, partial or total inhibition of viral protein processing or assembly, inhibition of viral entry into or exit from an infected cell, and/or clearance of the virus from a system via an immune response to the virus.

The invention provides, inter alia, compounds of the following structure:

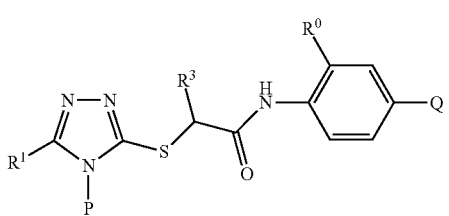

wherein P, Q, $R^1$, $R^3$ and $R^0$ are as defined above. In preferred embodiments, $R^1$ is selected from among Cl, Br, I, $CH_3$, $CF_3$, $CHF_2$, and $CH_2F$; $R^3$ is H; $R^0$ is selected from among Cl, Br, $CF_3$ and $CH_3$; and Q is CO2H or $SO_2NH_2$. In particularly preferred embodiments, $R^0$ is Cl.

P is preferably a substituted phenyl, naphthyl, 1,2,3,4-tetrahydronaphthyl, quinolinyl, isoquinolinyl, or cinnolinyl ring. In preferred embodiments, the group P is selected from among the moieties (a), (b), (c) and (d) below:

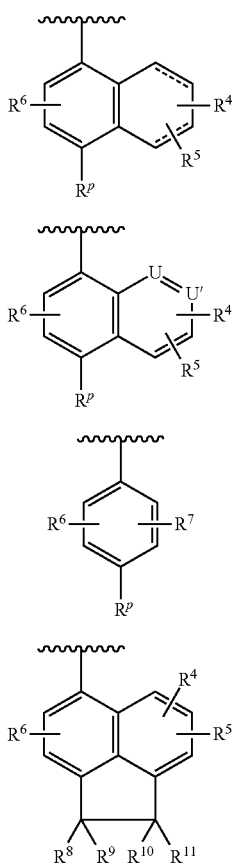

(a)

(b)

(c)

(d)

wherein $R^P$ is selected from among methyl, ethyl, propyl, isopropyl, cyclopropylmethyl, or $C_{3-6}$ cycloalkyl; $R^4$, $R^5$ and $R^6$ are independently selected from among H, F, Cl, Br, $CH_3$, $CF_3$, $CFH_2$, $CF_2H$, isopropyl, cyclopropyl, $OCH_3$, OH, $OCF_3$, $NH_2$ and $NHCH_3$.

U and U' are independently selected from N and CH; $R^7$ is selected from among Cl, Br, I, $CH_3$, $CF_3$, $OCH_3$, isopropyl, cyclopropyl, t-butyl, and cyclobutyl; and $R^8$-$R^{11}$ are independently H or $CH_3$. Preferably, when Q is $SO_2NH_2$, $R^1$ is not methyl unless $R^P$ is cyclopropyl or cyclopropylmethyl, and $R^7$ is methyl only when $R^6$ is also methyl.

Preferred classes of compounds are those having Structures 2 and 3 below:

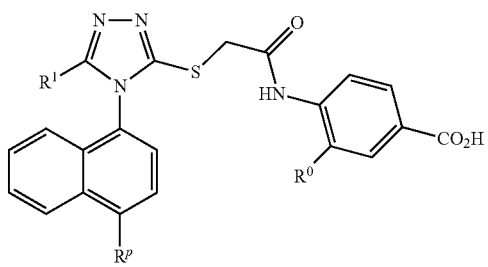

2

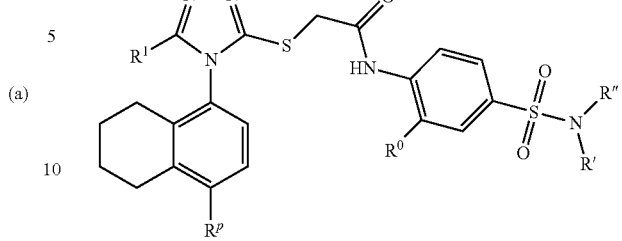

3 wherein $R^1$ is $CF_3$, $CHF_2$, $CH_2F$, or halogen; $R^0$ is halogen, $CF_3$ or methyl, R' and R" are independently H or an optionally substituted lower alkyl, $C_{1-5}$ acyl, or 1-($C_{2-4}$ acyloxy)$C_{1-4}$ alkoxyccarbonyl group, and $R^P$ is as defined above.

Particularly preferred classes of compounds correspond to structures 4 and 5

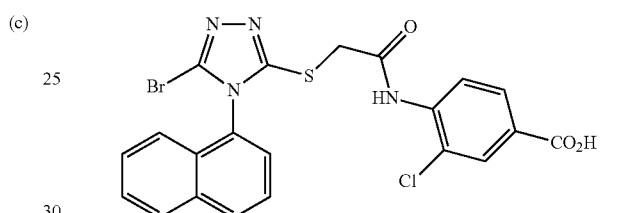

4

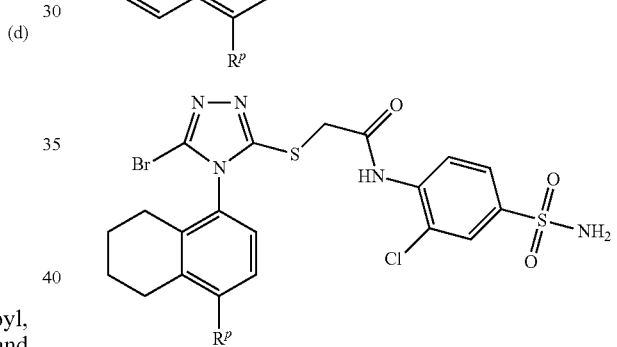

5 where $R^P$ is selected from methyl, ethyl, propyl, isopropyl, cyclopropyl, and cyclopropyl-methyl. It is most preferred that $R^P$ is ethyl or cyclopropyl. Compounds combining the features $R^1$=Br, $R^0$=Cl or $CH_3$, P=naphthyl or tetrahydronaphthyl, and Q=$CO_2$H or $SO_2$NR'R" exhibit surprisingly potent activity against RTs from a number of HIV isolates, combined with unexpectedly good pharmacokinetics in vivo.

Synthesis of Compounds

Synthesis of the compounds of the invention may be performed following procedures substantially as described in WO 2004/030611, WO 2004/050643, and U.S. Pat. No. 5,939,462. It should be recognized, however, that numerous alternative synthetic routes for the compounds of the invention are possible. The following exemplary routes are provided by way of example, for the guidance of practitioners skilled in the art of synthetic organic chemistry.

In one synthetic route, a suitably substituted aniline is amidated with an activated carboxylic acid compound (preferably a carbonyl halide), wherein the activated carboxylic acid compound further includes a leaving group $L_2$ (preferably bromine). After formation of the anilide, the reaction product is reacted with a mercaptotriazole (Het-SH), displacing the leaving group to form the desired compound as depicted in Scheme 1a below.

Scheme 1a

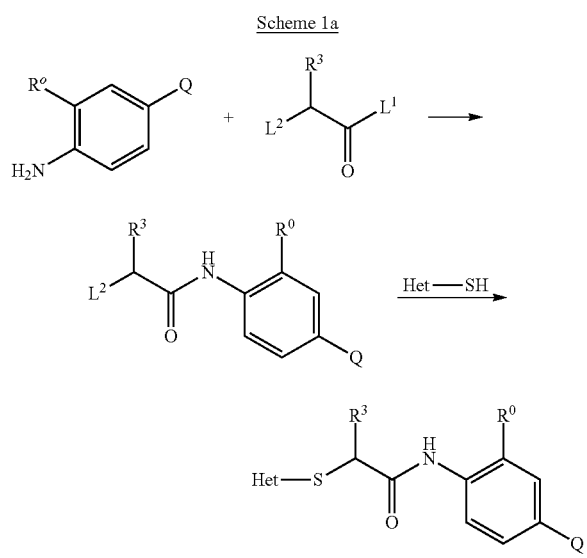

This scheme is advantageous where the mercaptotriazole "Het-SH" is valuable relative to the aniline, since the triazole is not used until the last step and is not subjected to the inevitable losses that occur during the synthetic manipulation of intermediates. The choice of leaving groups $L^1$ and $L^2$ will depend to some extent on the particular choice of amine and to a lesser degree on the particular mercaptotriazole. It is particularly preferred that $L^1$ and $L^2$ are halide, most preferably chloride or bromide. Suitable solvents for the amidation reaction include ethers, alcohols, and hydrocarbons (preferably halogenated) and the choice of suitable solvents will at least in part depend on the chemical nature of the reactants. With respect to the solvents, catalysts and/or bases employed in the above reaction, the considerations described by Connell et al. (U.S. Pat. No. 5,939,462) will generally apply.

An alternative general strategy is shown in Scheme 1b below. This approach involves the acylation of anilines with S-triazoly mercaptoacetic acids, which are readily prepared by alkylation of mercaptotriazoles with an α-haloacetic acid or ester.

Scheme 1b

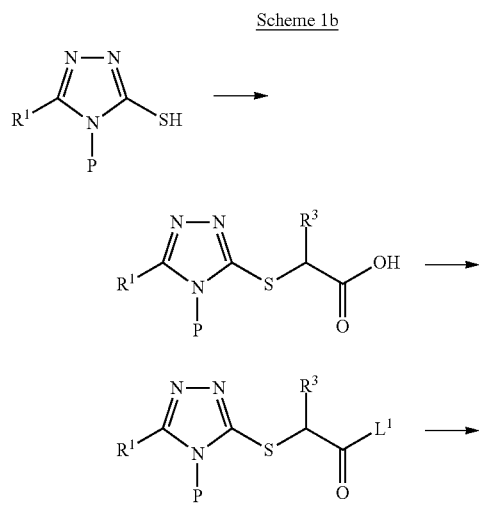

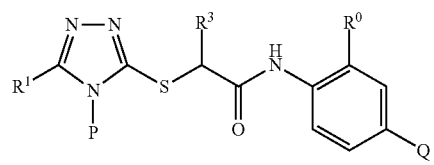

Suitable reagents include but are not limited to iodoacetic acid and methyl bromoacetate, and ethyl α-bromopropionate when it is desired that $R^3$ be methyl. If an ester is used, it is hydrolyzed after the S-alkylation to provide a free carboxylic acid. The acid and the aniline may be coupled with any of the usual carboxyl activating reagents or reagent mixtures, for example a carbodiimide in the presence of a tertiary amine base, optionally with N-hydroxybenzotriazole as catalyst, or thionyl or oxalyl chloride, with dimethylaminopyridine as catalyst. This scheme is advantageous when the aniline is valuable relative to the triazole.

An example of Scheme 1a is the synthesis outlined in Scheme 2, in which a compound of the invention is prepared from two separately-prepared precursors. The first precursor, comprising a substituted triazine, and the second precursor, comprising a substituted aniline, may be prepared following the protocols given below in the section entitled "Examples". Reaction of the precursors is typically carried out in a polar aprotic solvent such as DMF, in the presence of a base such as potassium carbonate.

Scheme 2

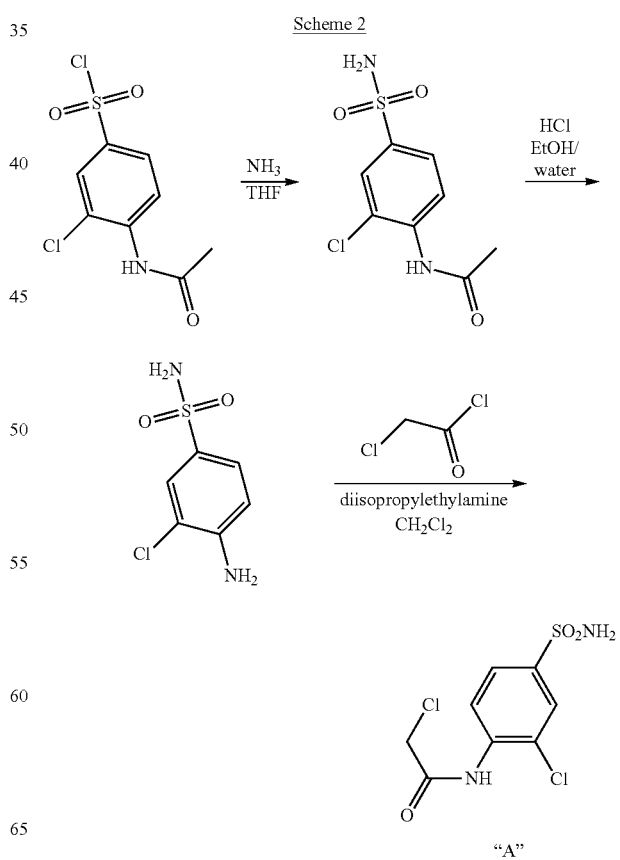

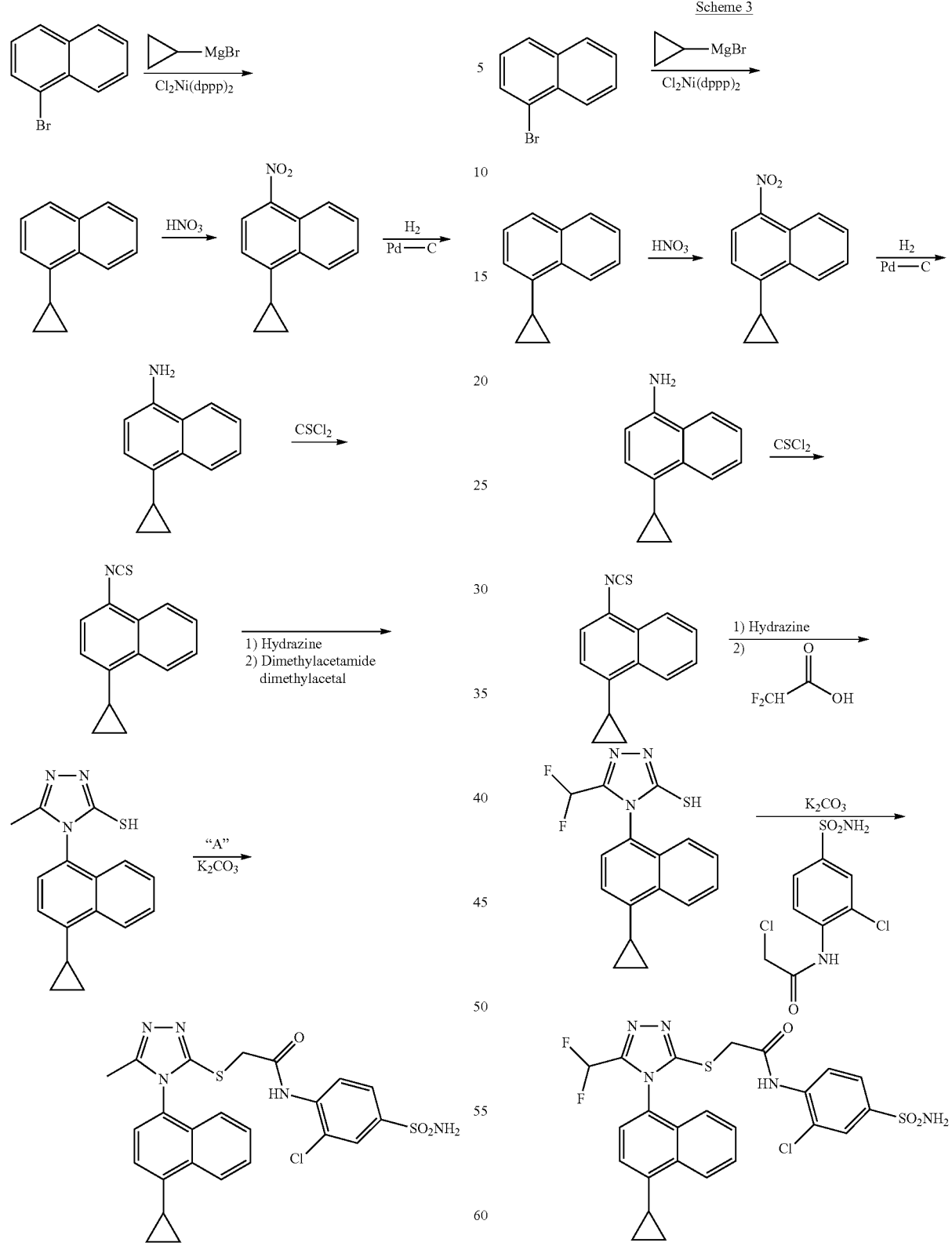

Where the triazine is substituted with a fluorinated alkyl group, a synthetic procedure as shown in Scheme 3 may be employed. A similar procedure is given below in the section entitled "Examples".

A halogen-substituted triazole may be prepared by dihalogenation of a triazole, followed by displacement of one of the halides, as shown in Scheme 4, which follows a procedure given below in the section entitled "Examples".

Scheme 4

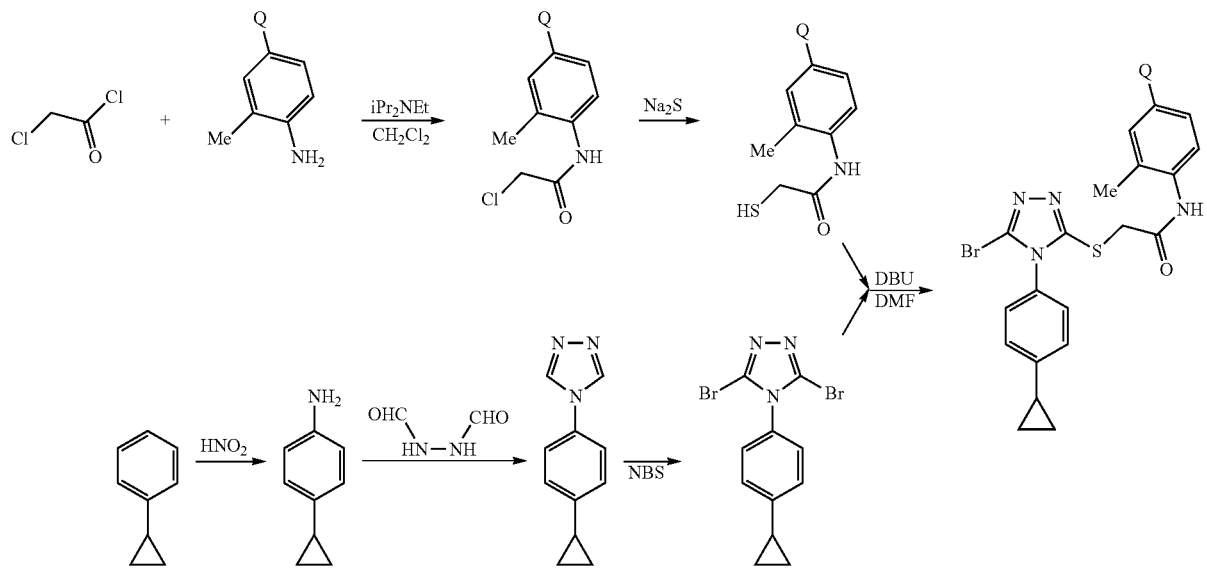

Another way to build a substituted triazole with a halogen is by diazotization of an aminotriazole, as shown in Scheme 5 below, which follows a procedure given below in the section entitled "Examples".

Scheme 5

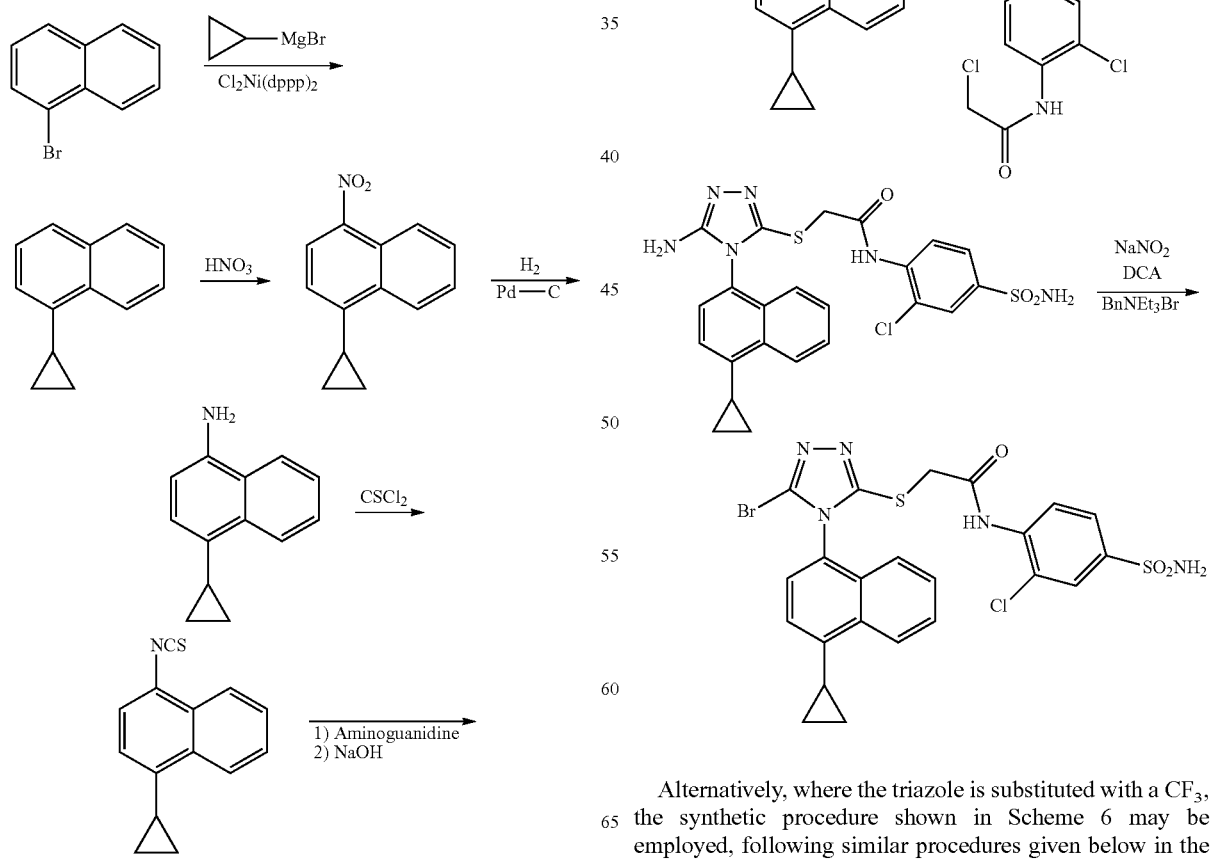

Alternatively, where the triazole is substituted with a CF$_3$, the synthetic procedure shown in Scheme 6 may be employed, following similar procedures given below in the section entitled "Examples".

Scheme 6

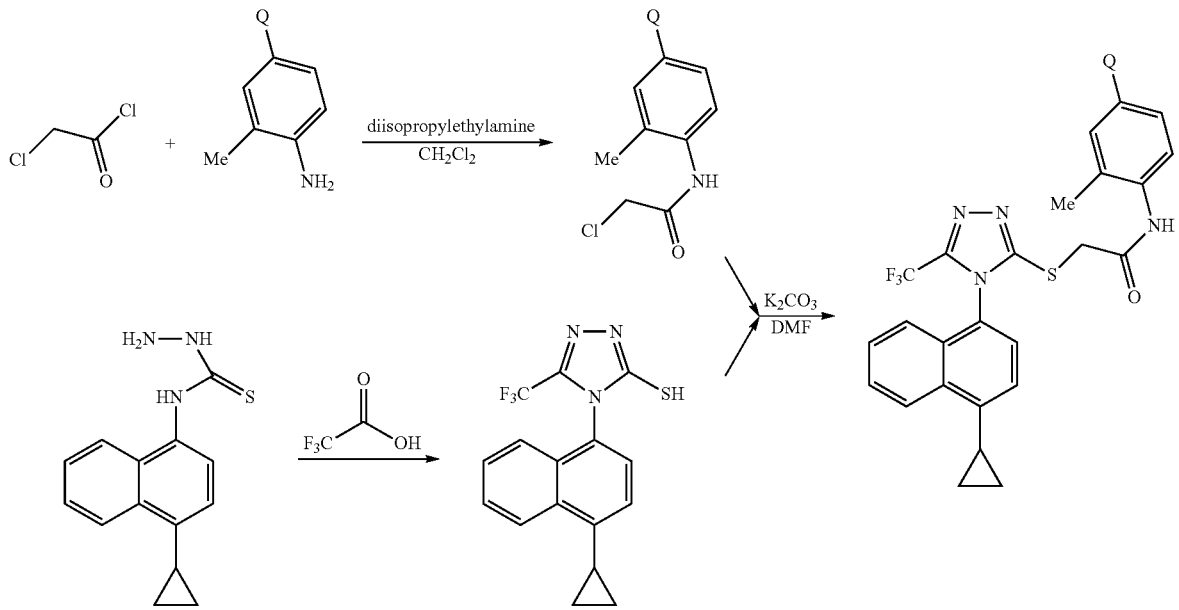

An example of the alternate synthetic approach outlined in Scheme 1a is shown in Scheme 7 below, wherein an aniline is acylated by a preformed S-triazolyl mercapto-acetic acid.

Scheme 7

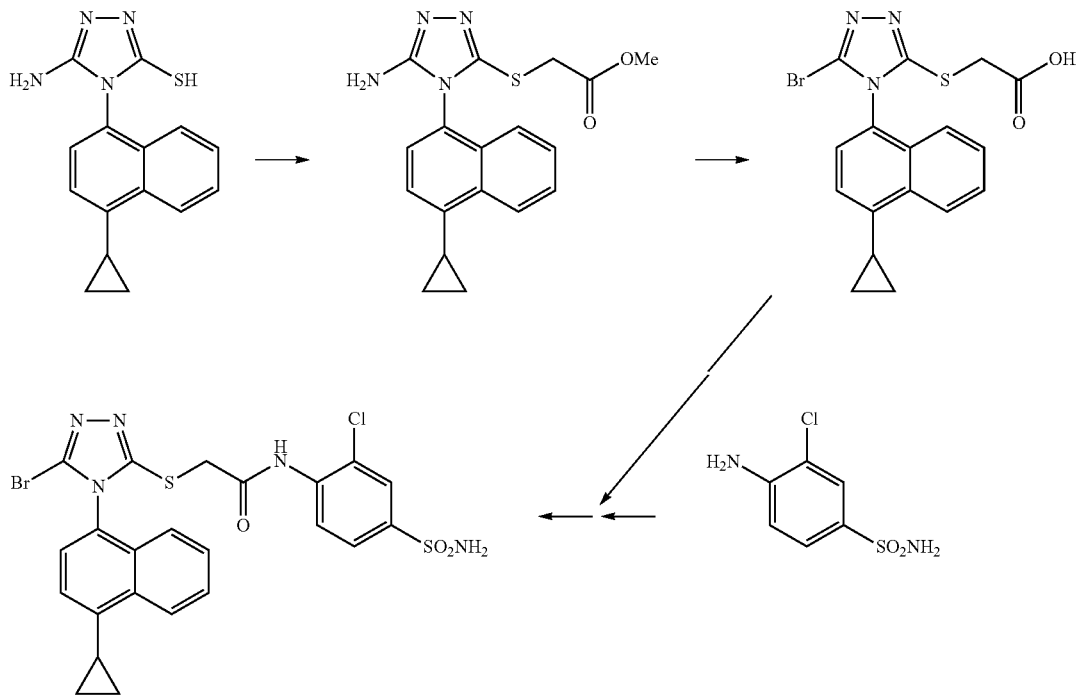

Pharmaceutical Compositions

Where compounds of the invention are administered as part of a pharmacological composition, it is contemplated that suitable compounds can be formulated in admixture with pharmaceutically acceptable carriers, excipients, and other additives. It is particularly preferred that the compounds of the invention are included in a pharmaceutical composition that is formulated with one or more non-toxic pharmaceutically acceptable carriers. The pharmaceutical compositions may be formulated for oral administration in solid or liquid form, for parenteral injection, or for rectal administration.

The pharmaceutical compositions of this invention can be administered to humans and other animals orally, rectally, parenterally, intravaginally, intraperitoneally, topically, bucally, or as an oral or nasal spray. The term "parenteral" administration as used herein refers to modes of administration which include but are not limited to intravenous, intramuscular, intraperitoneal, subcutaneous and intra-articular injection and infusion.

Pharmaceutical compositions for parenteral injection preferably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents and vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Compositions may also contain additives such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In order to prolong the effect of a compound of the invention, it may be desirable to slow the absorption of the drug from subcutaneous or intramuscular injection. This may be accomplished by the use of a liquid suspension of crystalline or amorphous material with poor water solubility. The rate of absorption of the compound then depends upon its rate of dissolution, which in turn may depend upon crystal size and crystalline form. Alternatively, delayed absorption of a parenterally-administered compound of the invention may be accomplished by dissolving or suspending the drug in an oil vehicle.

Injectable depot forms are made by forming unitary or microparticulate matrices of a compound of the invention in biodegradable polymers, including but not limited to polylactide-polyglycolide, poly(orthoesters), and poly(anhydrides). The rate of drug release can be controlled by varying the ratio of drug to polymer and the nature of the particular polymer employed. Depot injectable formulations may also prepared by entrapping the compound in liposomes or microemulsions which are compatible with body tissues.

Solid dosage forms for oral administration include but are not limited to capsules, tablets, pills, powders, dragees, and granules. In such solid dosage forms, the active compound is mixed with at least one inert, pharmaceutically acceptable excipient or carrier such as sodium citrate or dicalcium phosphate and/or (a) fillers or extenders, such as starches, lactose, sucrose, glucose, mannitol, and silicic acid, (b) binders, such as carboxymethylcellulose, alginates, gelatin, polyvinylpyrrolidone, sucrose, and acacia, (c) humectants, such as glycerol, (d) disintegrating agents, such as agar-agar, calcium carbonate, potato or tapioca starch, alginic acid, certain silicates, and sodium carbonate, (e) solution retarding agents, such as paraffin, (f) absorption accelerators, such as quaternary ammonium compounds, (g) wetting agents, such as cetyl alcohol and glycerol monostearate, (h) absorbents, such as kaolin and bentonite clay, and (i) lubricants, such as talc, calcium stearate, magnesium stearate, solid polyethylene glycols, sodium lauryl sulfate, and mixtures thereof. Solid dosage forms may also comprise buffering agents.

Solid compositions may also be employed as fillers in soft and hard-filled gelatin capsules using such excipients as lactose or milk sugar as well as high molecular weight polyethylene glycols and the like. The solid dosage forms can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally in a delayed manner. The active compounds may also be in micro-encapsulated form.

Liquid dosage forms for oral administration include pharmaceutically acceptable emulsions, solutions, suspensions, syrups and elixirs. In addition to the active compounds, the liquid dosage forms may contain inert diluents commonly used in the art such as, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral liquid compositions may also include adjuvants such as wetting agents, emulsifying and suspending agents, coloring, sweetening, flavoring, and perfuming agents.

Compositions for rectal or vaginal administration are preferably suppositories which can be prepared by mixing the compounds of this invention with suitable non-irritating excipients or carriers such as cocoa butter, polyethylene glycol or other suppository waxes which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are typically formed from mono- or multi-lamellar hydrated liquid crystals that are dispersed in an aqueous medium. Any non-toxic, physiologically acceptable lipid capable of forming liposomes may be used. Compositions in liposome form may contain, in addition to a compound of the present invention, membrane stabilizers, preservatives, excipients, and the like. The preferred lipids are phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the present invention may be used in the form of pharmaceutically acceptable salts derived from inorganic or organic acids. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences,* 1977, 66:1 et seq. The salts may be prepared in situ during the final isolation and purification of the compounds of the invention or separately by reacting a free base form with a suitable acid. Representative acid addition salts include, but are not limited to acetate, adipate, alginate, citrate, aspartate, benzoate, benzenesulfonate, bisulfate, butyrate, camphorate, camphorsulfonate, citrate, gluconate, glutamate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, 3-phenylpropionate, phosphate, pivalate, propionate, succinate, sulfate, tartrate, bicarbonate, p-toluenesulfonate and undecanoate. Basic nitrogen-containing groups may also be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

Basic addition salts can be prepared in situ during the final isolation and purification of compounds of this invention, or subsequently, by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, alkali and alkaline earth metals such as lithium, sodium, potassium, calcium, magnesium and aluminum salts and the like, and nontoxic quaternary ammonium and amine salts including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine, glucosamine, leucine, and the like.

Actual dosage levels of active ingredients in the pharmaceutical compositions of this invention may be varied so as to obtain an amount of the active compound(s) that is effective to achieve the desired therapeutic response for a particular patient, composition, and mode of administration. The selected dosage level will depend upon the activity of the particular compound, the route of administration, the dosing schedule, the severity of the condition being treated, and the condition and prior medical history of the patient being treated. Dose-ranging studies are routine, and it is within the ability of those skilled in the art to start doses of the compound at levels lower than required to achieve the desired therapeutic effect and to gradually increase the dosage until the desired effect is achieved. Generally, dosage levels of about 0.1 to about 100, more preferably about 5 to about 50 mg of an active compound per kilogram of body weight per day are administered orally to a mammalian patient. If desired, the effective daily dose may be divided into multiple doses for purposes of administration, e.g., two to four separate doses per day.

The compounds of the invention may be administered alone or in combination with other agents for the treatment of HIV. Particularly contemplated additional compounds include nucleoside-type reverse transcriptase inhibitors (e.g., lamivudine, zidovudine, stavudine, abacavir, tenofovir or didanosine), non-nucleoside reverse transcriptase inhibitors (e.g., nevirapine, delavirdine, efavirenz), protease inhibitors (e.g., ritonavir, saquinavir, indinavir, nelfmavir), fusion inhibitors (e.g., enfuvirtide), CCR5 antagonists, immunotherapeutic agents (e.g., ribavirin, IL-2), and active, passive, and/or therapeutic vaccines. Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect.

Therefore, the present invention provides pharmaceutical compositions comprising one or more compound having a structure according to any of formulae 1-5, as defined above, wherein the compound or compounds are present in a concentration effective to inhibit a reverse transcriptase and/or HIV replication in a cell of a patient when the composition is administered to the patient. In preferred embodiments, the pharmaceutical composition of the invention comprises one or more compounds according to any of formulae 2-5. It is particularly contemplated that a plurality of compounds may be incorporated into a single pharmaceutical composition, in order to obtain wide-ranging inhibition of a plurality of mutant RT enzymes.

With respect to suitable concentrations of contemplated compounds in pharmaceutical compositions, it should be appreciated that a person of ordinary skill in the art can readily adjust the amount of the compound to achieve inhibition of the reverse transcriptase and/or HIV replication. For example, inhibition of the HIV replication in a cell (typically a T-cell infected with the HIV virus) may be monitored in vitro using a blood culture and a luciferase based assay system as described below. Alternatively, inhibition of the reverse transcriptase may be monitored in vivo using RT-PCR to determine the amount of copies of viral DNA and/or RNA in blood or lymph nodes (containing HIV infected cells). It is generally contemplated that suitable concentrations will achieve a serum concentration of between 1 nM and 100 uM, and in some cases between 0.01 nM and 1 nM).

EXAMPLES

The following experiments are provided only by way of example, and should not be understood as limiting the scope of the invention.

Compounds of the Invention

2-[5-Bromo-4-(4-cyclopropylnaphthalen-1-yl)-4H-[1,2,4]triazol-3-ylsulfanyl]-N-(2-chloro-4-sulfamoylphenyl)acetamide (Method A)

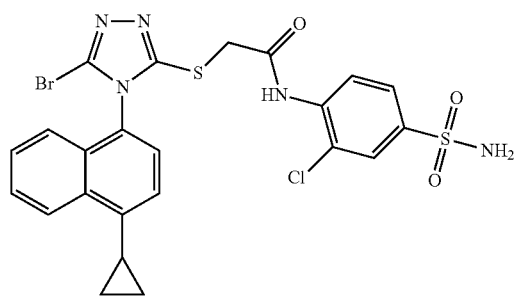 [SMILES: NS(=O)(=O)c1ccc(NC(=O)CSc2nnc(Br)n2-c2ccc(C3CC3)c3ccccc23)c(Cl)c1]

1-Cyclopropyl-naphthalene

Cyclopropylmagnesium bromide (150 mL, 0.5 M in tetrahydrofuran) was slowly added to a solution of 1-bromonaphthalene (10 g, 50 mmol) and [1,3-bis(diphenylphosphino)propane]dichloronickel(II) in tetrahydrofuran (10 mL) stirred at 0° C. The reaction mixture was stirred at room temperature for 16 hours and the solvent was evaporated under reduced pressure. EtOAc and ammonium chloride in water were added. After extraction, the organic layer was dried over sodium sulfate, filtered and concentrated under reduced pressure. The residue was purified by silica gel chromatography to yield 1-cyclopropyl-naphthalene (6.4 g, 76%).

1-Cyclopropyl-4-nitro-naphthalene

Sodium nitrite (30 mL) was slowly added (over 2 hours) to 1-cyclopropyl-naphthalene (6.4 g, 38 mmol) stirred at 0° C. The reaction mixture was stirred at 0° C. for an extra 30 min and then was slowly poured into ice. Water was added, followed by EtOAc. After extraction, the organic layer was washed with a 1% aqueous solution of NaOH, then washed with water, dried over sodium sulfate, filtered and concentrated under reduced pressure. The residue was purified by silica gel chromatography to yield 1-cyclopropyl-4-nitro-naphthalene (5.2 g, 64%).

1-Amino-4-cyclopropyl-naphthalene

A solution of 1-cyclopropyl-4-nitro-naphthalene (5 g, 23 mmol) in ethanol (200 mL) was stirred under hydrogen in the presence of Pd/C (10% net, 1.8 g). The reaction mixture was shaken overnight, then filtered over celite. The solvent was evaporated, and the residue was purified by silica gel chromatography to yield 1-amino-4-cyclopropyl-naphthalene (3.1 g, 73%).

1-Cyclopropyl-4-isothiocyanato-naphthalene

Thiophosgene (1.1 g, 9.7 mmol) was added to a solution of 1-amino-4-cyclopropyl-naphthalene (1.8 g, 9.7 mmol) and diisopropylethylamine (2 eq) in dichloromethane (50 mL) stirred at 0° C. The reaction mixture was stirred for 5 min at this temperature, then a 1% solution of HCl in water was added and the organic layer was separated, washed with brine, dried over sodium sulfate, filtered and the solvent was evaporated under reduced pressure. Hexane was added, and the resulting precipitate was filtered. The solvent was evaporated to yield 1-cyclopropyl-4-isothiocyanatonaphthalene (1.88 g, 86%).

5-Amino-4-(4-cyclopropylnaphthalen-1-yl)-4H-[1,2,4]triazole-3-thiol

A mixture of aminoguanidine hydrochloride (3.18 g, 29 mmol), 1-cyclopropyl-4-isothiocyanato-naphthalene (3.24 g, 14 mmol) and diisopropylethylamine (3 eq) in DMF (20 mL) was stirred at 50° C. for 15 hours. The solvent was evaporated, toluene was added, and the solvent was evaporated again. A 2.0 M aqueous solution of sodium hydroxide (30 mL) was added and the reaction mixture was heated at 50° C. for 60 hours. The reaction mixture was filtered, and the filtrate was neutralized with a 2.0 M aqueous solution of HCl. New filtration, then evaporation of solvent and purification of the residue by silica gel chromatography to yield 5-amino-4-(4-cyclopropylnaphthalen-1-yl)-4H-[1,2,4]triazole-3-thiol (2.0 g, 49%).

2-[5-Amino-4-(4-cyclopropylnaphthalen-1-yl-4H-[1,2,4]triazol-3-ylsulfanyl)-N-(2-chloro-4-sulfamoylphenyl)Acetamide In a solution of 5-amino-4-(4-cyclopropylnaphthalen-1-yl)-4H-[1,2,4]triazole-3-thiol (708 mg, 2.5 mmol), K₂CO₃ (380 mg, 2.5 mmol) in DMF (20 mL) was added 2-chloro-N-(2-chloro-4-sulfamoylphenyl)acetamide (710 mg, 2.5 mmol). The reaction mixture was stirred at room temperature overnight. Upon completion of the reaction, the solvent was evaporated. The residue was purified by silica gel chromatography to yield 2-[5-Amino-4-(4-cyclopropylnaphthalen-1-yl)-4H-[1,2,4]triazol-3-ylsulfanyl]-N-(2-chloro-4-sulfamoylphenyl)acetamide (1.26 g, 95%).

2-[5-Bromo-4-(4-cyclopropylnaphthalen-1-yl]-4H-[1,2,4]triazol-3-ylsulfannyl]-N-(2-chloro-4-sulfamoylphenyl)acetamide Dichloroacetic acid (180 uL, 2.2 mmol) was added to a suspension of 2-[5-amino-4-(4-cyclopropylnaphthalen-1-yl)-4H-[1,2,4]triazol-3-ylsulfanyl]-N-(2-chloro-4-sulfamoylphenyl)acetamide (0.59 g, 1.1 mmol), sodium nitrite (1.5 g, 22 mmol) and BTEABr (0.91 g, 3.3 mmol) in dibromomethane (30 mL). The reaction mixture was stirred at room temperature for 4 hours, then extracted with dichloromethane and sodium bicarbonate in water. The organic layer was dried over sodium sulfate, filtered and concentrated under reduced pressure. The residue was purified by silica gel chromatography to yield 2-[5-bromo-4-(4-cyclopropylnaphthalen-1-yl)-4H-[1,2,4]triazol-3-ylsulfanyl]-N-(2-chloro-4-sulfamoylphenyl)acetamide (224 mg, 31%).

2-[5-Bromo-4-(4-cyclopropylnaphthalen-1-yl)-4H-[1,2,4]triazole-3-ylsulfanyl]-N-(2-chloro-4-sulfamoylphenyl)acetamide (Method B)

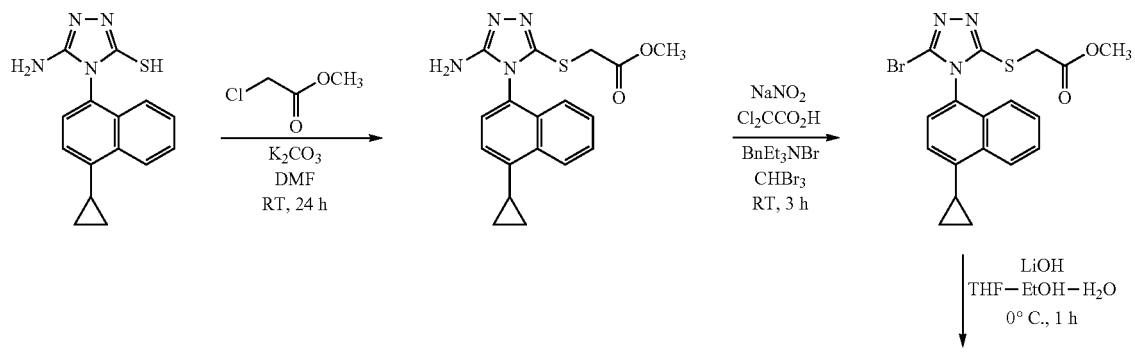

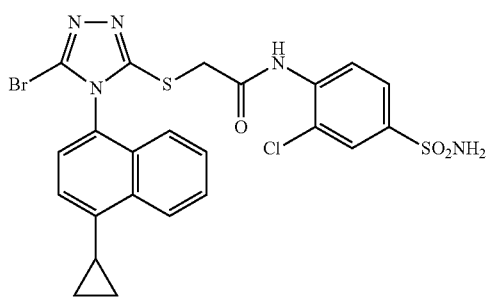 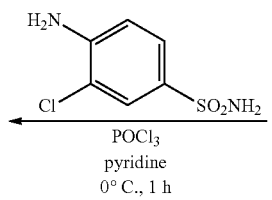 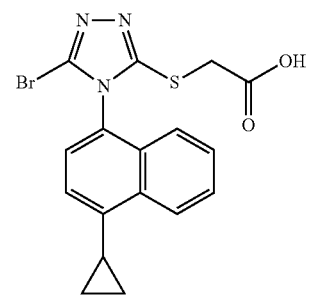

POCl₃
pyridine
0° C., 1 h

2-[5-Amino-4-(4-cyclopropylnaphthalen-1-yl)-4H-[1,2,4]triazol-3-ylsulfanyl]acetic acid methyl ester

| Materials | Amount | Mol. Wt. | mmoles |
|---|---|---|---|
| thiotriazole | 2.24 g | 282.36 | 7.9 |
| methyl chloroacetate | 0.73 ml | 108.52 | 8.3 (1.05 eq) |
| potassium carbonate | 1.21 g | 138.21 | 8.7 (1.1 eq) |
| dimethylformamide | 40 ml | | (5 mL/mmol) |

Procedure:

To a suspension of thiotriazole and potassium carbonate in DMF was added methyl chloroacetate dropwise at room temperature for 5 min. The reaction was stirred at room temperature for 24 h and slowly poured into a stirred ice-cold water solution. The tan precipitate was collected by vacuum filtration and dried under high vacuum at 50° C. for 16 h in the presence of $P_2O_5$ to yield 2.24 g (80%) of the title compound.

2-[5-Bromo-4-(4-cyclopropylnaphthalen-1-yl)-4H-[1,2,4]triazol-3-ylsulfanyl]acetic acid methyl ester

| Materials | Amount | Mol. Wt. | mmoles |
|---|---|---|---|
| thiotriazole L10183-58 | 709 mg | 354.43 | 2.0 |
| bromoform | 10 ml | | (5 ml/mmol) |
| sodium nitrite | 2.76 g | 69.00 | 40 (20 eq) |
| benzyltriethylammonium bromide | 1.63 g | 272.24 | 6.0 (3 eq) |
| dichloroacetic acid | 0.33 ml | 28.94 | 4.0 (2 eq) |

Procedure:

To a solution of 2-[5-amino-4-(4-cyclopropylnaphthalen-1-yl)-4H-[1,2,4]triazol-3-ylsulfanyl]acetic acid methyl ester and benzyltriethylammonium chloride in bromoform was added sodium nitrite. To the mixture was added dichloroacetic acid and the reaction mixture was stirred at room temperature for 3 h. The mixture was directly loaded onto a 7-inch column of silica gel that was packed with $CH_2Cl_2$. The column was first eluted with $CH_2Cl_2$ until all $CHBr_3$ eluted, and was then eluted with acetone/$CH_2Cl_2$ (5:95) to give 713 mg (85%) of the title compound.

2-[5-Bromo-4-(4-cyclopropylnaphthalen-1-yl)-4H-[1,2,4]triazol-3-ylsulfanyl]acetic acid

| Materials | Amount | Mol. Wt. | mmoles |
|---|---|---|---|
| thiotriazole methyl ester | 1.14 g | 418.31 | 2.7 |
| tetrahydrofuran | 10 ml | | (~3 ml/mmol) |
| ethanol | 10 ml | | (~3 ml/mmol) |
| water | 10 ml | | (~3 ml/mmol) |
| lithium hydroxide | 98 mg | 23.95 | 4.1 (1.5 eq) |

Procedure:

To a solution of 2-[5-bromo-4-(4-cyclopropylnaphthalen-1-yl)-4H-[1,2,4]triazol-3-ylsulfanyl]acetic acid methyl ester, in a mixture of THF and EtOH at 0° C., was added a solution of LiOH in $H_2O$ dropwise over 5 min. The reaction was complete after stirring at 0° C. for an additional 45 min. The reaction was neutralized to pH 7 by the addition of 0.5 N HCl solution at 0° C., and the resulting mixture was concentrated in vacuo to ⅕th of its original volume. The mixture was diluted with $H_2O$ (~20 mL) and acidified to pH 2-3 by the addition of 0.5 N HCl to produce sticky solid. (If the product comes out as an oil during acidification, extraction with $CH_2Cl_2$ is recommended.) The tan solid was collected by vacuum filtration and dried under high vacuum at 50° C. for 16 h in the presence of $P_2O_5$ to yield 1.02 g (93%) of the title compound.

2-[5-Bromo-4-(4-cyclopropylnaphthalen-1-yl)-4H-[1,2,4]-triazole-3-ylsulfanyl]-N-(2-chloro-4-sulfamoylphenyl)acetamide

| Materials | Amount | Mol. Wt. | mmoles |
|---|---|---|---|
| thiotriazole carboxylic acid | 884 mg | 404.28 | 2.2 |
| 4-amino-3-chlorophenylsulfonamide | 452 mg | 206.65 | 2.2 |
| pyridine | 22 ml | | (10 ml/mmol) |
| phosphorus oxychloride | 0.24 ml | 153.33 | 2.6 (1.2 eq) |

Procedure:

To a solution of the carboxylic acid and aniline shown above, in pyridine at 0° C., was added POCl₃ dropwise for 5 min. The reaction was complete after stirring at 0° C. for an additional 50 min. The reaction mixture was quenched by addition of $H_2O$ (1 mL), then concentrated in vacuo to light brown oil which was diluted with $CH_2Cl_2$ (200 ml). The organic layer was washed with H₂O (1×50 ml), saturated NaHCO₃ solution (1×50 ml), then brine (1×50 ml). The organic solution was dried over Na₂SO₄ and concentrated to dryness. The resulting oil was triturated with EtOH to give light yellow solid. To the mixture was added H₂O to collect more solid. The light yellow solid was collected by vacuum filtration and dried under high vacuum for 16 hrs to yield 930 mg (72%) of product. Additional product (132 mg, 10%) was recovered by extraction of the filtrate with CH₂Cl₂ followed by column chromatography with acetone/CH₂Cl₂ (20:80).

2-[5-Bromo-4-(4-cyclopropyl-7-methoxynaphthalen-1-yl)-4H-[1,2,4]-triazole-3-ylsulfanyl]N-(2-chloro-4-sulfamoylphenyl)acetamide

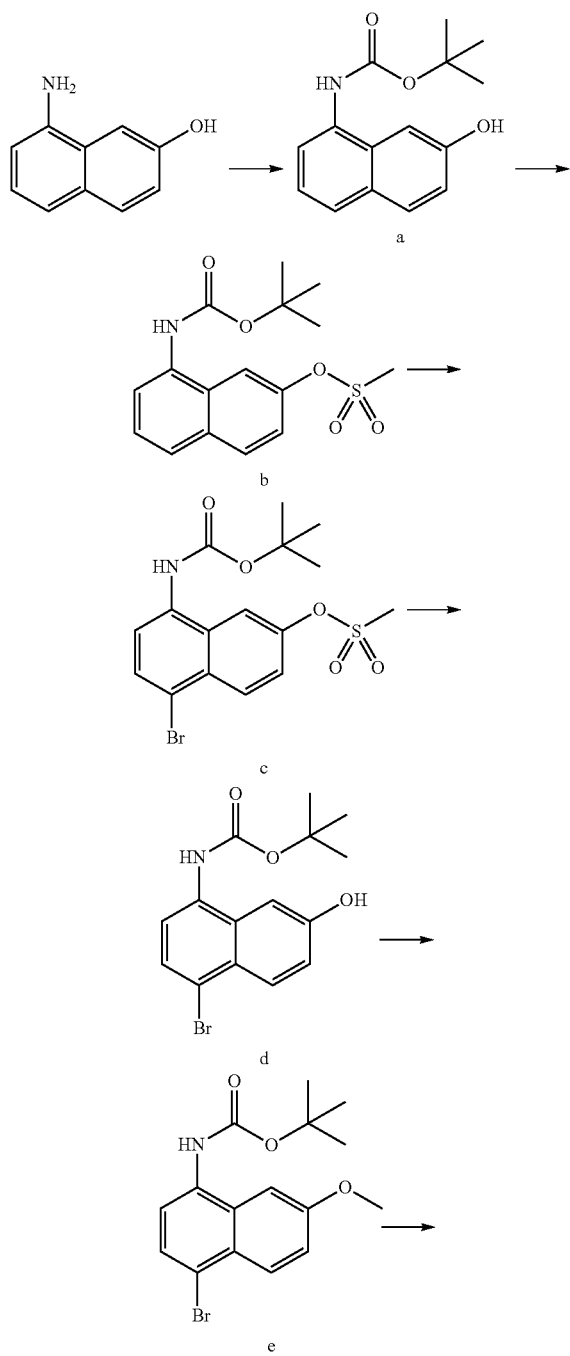

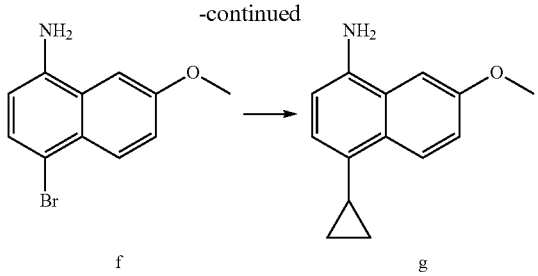

1-amino-4-cyclopropyl-7-methoxynaphthalene

To a stirred solution of 8-amino-2-naphthol (5 g, 31.4 mmol) in a mixture of tetrahydrofuran (50 mL) and dichloromethane (100 mL) was added di-t-butyldicarbonate (6.86 g, 31.4 mmol). The mixture was stirred at 70° C. for 18 hours. After the mixture was cooled to room temperature, saturated aqueous sodium carbonate was added and the product was extracted with dichloromethane. The organic layer was washed with water and brine, dried over sodium sulfate, filtered and concentrated under reduced pressure. The obtained residue was purified by silica gel column chromatography (dichloromethane:ethyl acetate, 9:1) to afford the N-BOC derivative a. (4.85 g, 60% yield)

To a mixture of the N-BOC derivative a (4.85 g, 18.7 mmol) and triethylamine (3.91, 28.1 mmol) in dichloromethane (170 mL) was added methanesulfonic anhydride (3.58 g, 20.6 mmol) at 0° C. The mixture was stirred for 30 min and poured into saturated aqueous sodium bicarbonate solution. The organic layer was extracted with dichloromethane, dried over sodium sulfate, filtered and concentrated under reduced pressure to give the methanesulfonate ester b. (6.22 g, quantitative yield)

To a solution of methanesulfonate b (6.12 g, 18.1 mmol) in 150 mL of acetic acid was added N-bromosuccinimide (3.39 g, 19 mmol). The mixture was stirred for 2 h and water and dichloromethane were added. The aqueous layer was adjusted to pH 7 by addition of 10 N aqueous sodium hydroxide. The organic layer was extracted with dichloromethane, dried over sodium sulfate, filtered and concentrated under reduced pressure to give the crude 5-bromo derivative c. (7.6 g, quantitative yield)

A mixture of c (7.72 g, 18.5 mmol) and 10% aqueous sodium hydroxide solution (370 mL) in tetrahydrofuran (220 mL) was stirred at 50° C. for 5 days. The mixture was cooled to 0° C. and neutralized with concentrated hydrochloric acid. The mixture was concentrated under reduced pressure, and the product was extracted with ethyl acetate. The organic layer was dried over sodium sulfate, filtered and concentrated to give the naphthol d. (5.87 g, 94% yield)

A mixture of naphthol d (3.53 g, 10.4 mmol), methyl iodide (0.65 mL, 10.4 mmol) and sodium hydroxide (417 mg, 10.4 mmol) in acetone (25 mL) was stirred at room temperature for 4 hours. The resulting mixture was concentrated and the residue purified by column chromatography (85% hexane/15% ethyl acetate) to afford 2.39 g, 65% yield of the methyl ether e.

A mixture of methyl ether e (3.25 g, 9.22 mmol) in 4N HCl in 1,4-dioxane (92 mL) was stirred at room temperature for 1 hour. The mixture was concentrated under reduced pressure and was added ethyl acetate and saturated sodium bicarbonate solution. The extracted organic layer was washed with water and brine, dried over sodium sulfate and concentrated under reduced pressure to give 2-methoxy-5-bromo-8-aminonaphthalene f (2.14 g, 92% yield)

To a solution of aminonaphthalene f (1 g, 4.0 mmol), cyclopropyl boronic acid (438 mg, 5.1 mmol), potassium phosphate (2.97 g, 14 mmol) and tricyclohexylphosphine (112 mg, 0.4 mmol) in toluene (21 mL) and water (0.8 mL) under nitrogen atmosphere was added palladium acetate (45 mg, 0.2 mmol) with vigorous stirring. The mixture was heated to 100° C. for 3 h and then cooled to room temperature. Water was added and the mixture extracted with ethyl acetate, dried over sodium sulfate and concentrated.

Purification by column chromatography (50% hexane/50% ethyl acetate) afforded the title compound g. (699 mg, 82% yield)

Compound g (699 mg, 3.28 mmol) was dissolved in 18 mL of dichloromethane. Sodium bicarbonate (9 mL, sat. solution) and thiophosgene (0.25 mL, 3.28 mmol) were added and the mixture stirred at room temperature for 1 h. The organic layer was separated, dried over sodium sulfate and concentrated to afford 819 mg, 98% yield of compound h which was used in the next step without further purification.

Compound h (819 mg, 3.21 mmol) was dissolved in 6 mL of dimethylformamide, aminoguanidine hydrochloride salt (532 mg, 4.8 mmol) and diisopropyl ethylamine (0.84 mL, 4.8 mmol) were added, and the mixture was stirred at 50° C. for 18 hours. The mixture was then concentrated and to the residue was added 2M aqueous sodium hydroxide solution (10 mL). The mixture was stirred at 50° C. for 18 hours and then cooled to room temperature. The resulting mixture was then neutralized with aqueous 1N HCl and the precipitate collected to give compound i. (200 mg, 25% yield)

Compounds i (63 mg, 0.2 mmol) and/(57 mg, 0.2 mmol) were dissolved in DMF (2 mL) and potassium carbonate (30 mg, 0.2 mmol) was added. The mixture was stirred at room temperature for 18 hours. Water was then added to the mixture and the precipitate formed collected to give 70 mg (57%) of compound k.

Dichloroacetic acid (0.05 mL, 0.226 mmol) was added to a mixture of compound k (63 mg, 0.113 mmol), benzyltriethyl ammonium bromide (93 mg, 0.34 mmol) and sodium nitrite (156 mg, 2.26 mmol) in dibromomethane (5 mL). The mixture was stirred at room temperature for 18 hours in the dark. The reaction mixture was then concentrated and the resulting residue was purified by prep. TLC (95% dichloromethane/5% methanol) to afford 13.8 mg of the sulfonic acid and 2 mg of title compound l.

2-[5-Bromo-4-(4-cyclopropyl-2-methylnaphthalen-1-yl)-4H-[1,2,4]-triazole-3-ylsulfanyl]-N-(2-chloro-4-sulfamoylphenyl)acetamide

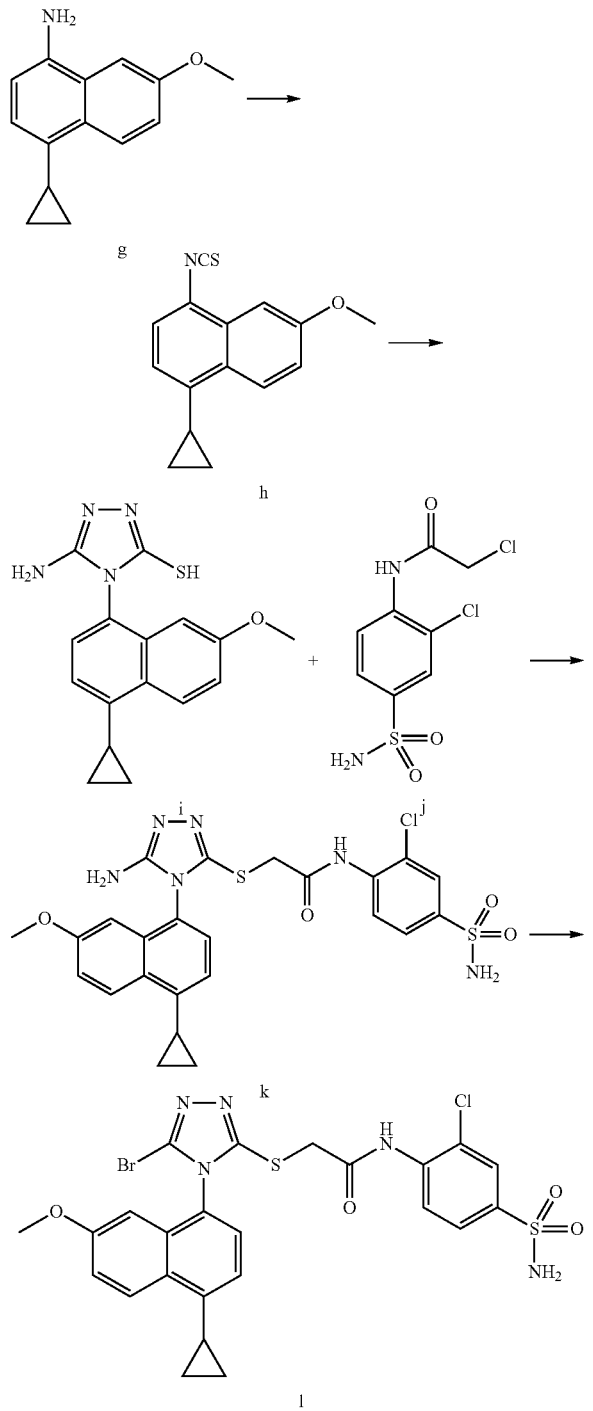

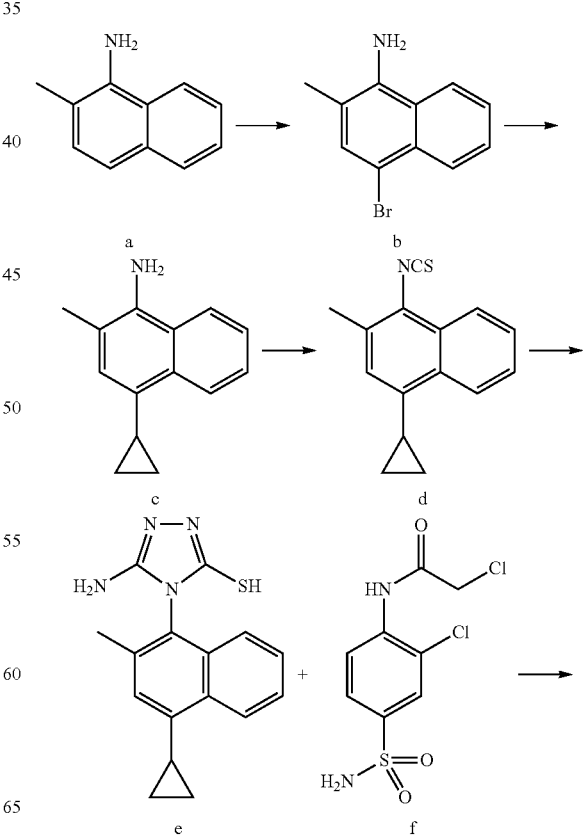

-continued

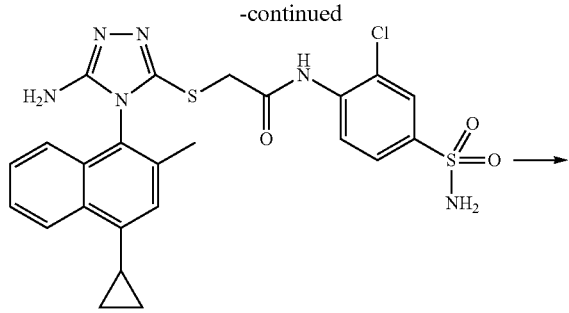

g

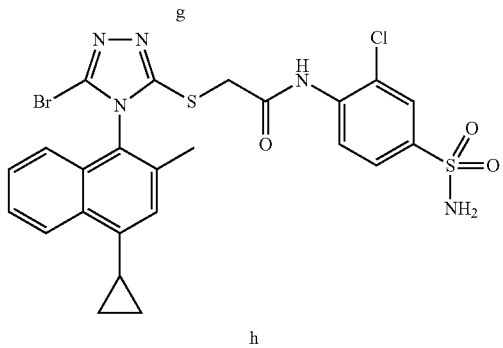

h

To a stirred solution of 2-methyl-1-aminonaphthalene a (7.5 g, 47.7 mmol) in tetrahydrofuran (225 mL) was added N-bromosuccinimide (10 g, 56.2 mmol) at 0° C. The mixture was stirred at room temperature for 4 hours. Water was added to the mixture and the product was extracted with ethyl acetate. The organic layer was washed with water and brine, dried over sodium sulfate, filtered and concentrated under reduced pressure. The resulting residue was purified by column chromatography (75% hexane/25% ethyl acetate) to afford 4.73 g, 42% yield of compound b.

To a solution of b (1 g, 4.24 mmol), cyclopropyl boronic acid (472 mg, 5.5 mmol), potassium phosphate (3.14 g, 14.8 mmol) and tricyclohexylphosphine (118 mg, 0.42 mmol) in toluene (22 mL) and water (0.85 mL) under nitrogen atmosphere was added palladium acetate (47 mg, 0.21 mmol). The mixture was heated to 100° C. for 3 h and then cooled to room temperature. Water was added and the mixture extracted with ethyl acetate, dried over sodium sulfate and concentrated. Purification by column chromatography (90% hexane/10% ethyl acetate) afforded compound c. (728 mg, 87% yield)

Compound c (728 mg, 3.7 mmol) was dissolved in 18 mL of dichloromethane. Sodium bicarbonate (9 mL, sat. solution) and thiophosgene (0.28 mL, 3.7 mmol) were added and the mixture stirred at room temperature for 1 h. Then, the organic layer was separated, dried over sodium sulfate and concentrated to afford 877 mg, 99% yield of compound d which was used in the next step without further purification.

Compound d (877 mg, 3.7 mmol) was dissolved in 6 mL of dimethylformamide, aminoguanidine hydrochloride salt (608.5 mg, 5.5 mmol) and diisopropyl ethylamine (1.0 mL, 5.5 mmol) were added and the mixture stirred at 50° C. for 18 hours. The mixture was concentrated and to the resulting residue was added 2M aqueous sodium hydroxide solution (15 mL). The mixture was stirred at 50° C. for 18 hours and then cooled to room temperature. The resulting mixture was then neutralized with aqueous 1N HCl and the precipitate collected to give compound e. (472 mg, 50% yield)

Compounds e (100 mg, 0.34 mmol) and f (96 mg, 0.34 mmol) were dissolved in DMF (2 mL) and potassium carbonate (51 mg, 0.37 mmol) was added. The mixture was stirred at room temperature for 18 hours. Water was then added to the mixture and the precipitate formed collected and purified by prep. TLC (90% dichloromethane/10% methanol) to give 83 mg, 45% yield of compound g.

Dichloroacetic acid (0.03 mL, 0.31 mmol) was added to a mixture of compound g (83 mg, 0.15 mmol), benzyltriethyl ammonium bromide (125 mg, 0.46 mmol) and sodium nitrite (211 mg, 3.06 mmol) in dibromomethane (5 mL). The mixture was stirred at room temperature for 18 hours in the dark. The reaction mixture was then concentrated and the resulting residue was purified by prep. TLC (95% dichloromethane/5% methanol) to afford 55.7 mg of the sulfonic acid and 7 mg of title compound h.

2-[5-Bromo-4-(2-chloro-4-cyclopropylphenyl)-4H-[1,2,4]-triazole-3-ylsulfanyl]-N-(2-chloro-4-sulfamoylphenyl)acetamide

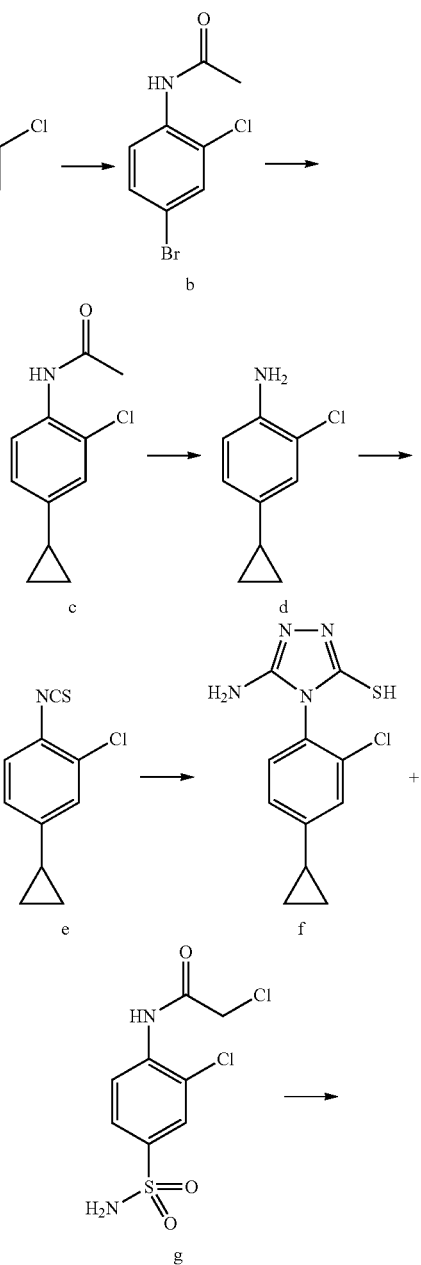

-continued

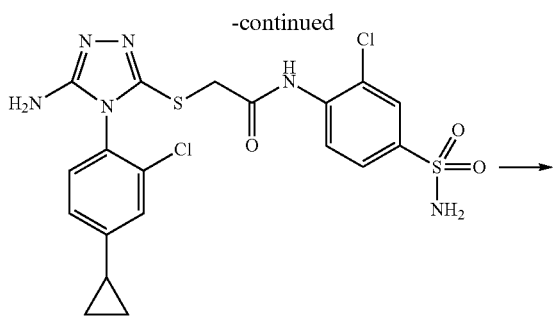

h

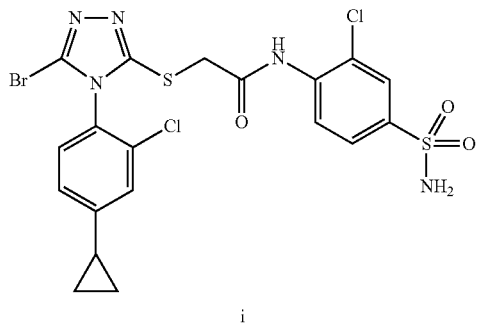 [SMILES: NS(=O)(=O)c1ccc(NC(=O)CSc2nnc(Br)n2-c2ccc(C3CC3)cc2Cl)c(Cl)c1]

i

Compound a (1 g, 4.8 mmol) was dissolved in 10 mL of anhydrous methylene chloride. To this mixture was added triethylamine (0.68 mL, 4.8 mmol) and the reaction was stirred at room temperature for 5 min. Acetyl chloride (0.5 mL, 7.2 mmol) was then added at 0° C. and the mixture stirred at room temperature for 2 hours. Water and dichloromethane were added and the layers separated. The organic layer was then dried over sodium sulfate and concentrated to give 1.11 g, 92% yield of compound b.

To a solution of b (500 mg, 2.01 mmol), cyclopropyl boronic acid (225 mg, 2.62 mmol), potassium phosphate (1.49 g, 7.04 mmol) and tricyclohexylphosphine (56 mg, 0.2 mmol) in toluene (10 mL) and water (0.4 mL) under nitrogen atmosphere was added palladium acetate (23 mg, 0.1 mmol). The mixture was heated to 100° C. for 3 h and then cooled to room temperature. Water was added and the mixture extracted with ethyl acetate, dried over sodium sulfate and concentrated to give 550 mg of crude product c that was used in the next step without further purification.

Compound c (500 mg, 2.4 mmol) was dissolved in 4 mL of ethanol. Aqueous 1N HCl (4 mL) was added and the mixture stirred at reflux for 8 hours. The solvent was removed in vacuo to afford 440 mg of compound d which was used in the next step without further purification.

Compound d (440 mg, 2.6 mmol) was dissolved in 14 mL of dichloromethane. Sodium bicarbonate (7 mL, sat. solution) and thiophosgene (0.2 mL, 2.6 mmol) were added and the mixture stirred at room temperature for 1 h. Then, the organic layer was separated, dried over sodium sulfate and concentrated to afford 877 mg, 99% yield of compound e which was used in the next step without further purification.

Compound e (447 mg, 2.1 mmol) was dissolved in 3 mL of dimethylformamide, aminoguanidine hydrochloride salt (355 mg, 3.2 mmol) and diisopropyl ethylamine (0.56 mL, 3.2 mmol) were added and the mixture stirred at 50° C. for 18 hours. The mixture was then concentrated and to the resulting residue was added 2M aqueous sodium hydroxide solution (10 mL). The mixture was stirred at 50° C. for 18 hours and then cooled to room temperature. The resulting mixture was then neutralized with aqueous 1N HCl and the precipitate (product) collected to give compound f (240 mg, 44% yield)

Compounds f (89 mg, 0.33 mmol) and g (94 mg, 0.33 mmol) were dissolved in DMF (1.5 mL) and potassium carbonate (51 mg, 0.37 mmol) was added. The mixture was stirred at room temperature for 18 hours. Water was then added to the mixture and the precipitate formed collected and purified by prep. TLC (90% dichloromethane/10% methanol) to give 116 mg, 68% yield of compound h.

Dichloroacetic acid (0.04 mL, 0.46 mmol) was added to a mixture of compound h (116 mg, 0.23 mmol), benzyltriethyl ammonium bromide (183 mg, 0.68 mmol) and sodium nitrite (304 mg, 4.6 mmol) in dibromomethane (5 mL). The mixture was stirred at room temperature for 18 hours in the dark. The reaction mixture was then concentrated and the resulting residue was purified by prep. TLC (95% dichloromethane/5% methanol) to afford 99.10 mg of the sulfonic acid and 17.90 mg of title compound i.

4-(2-(5-bromo-4-(2-chloro-4-cyclopropyl-6-methylphenyl)-4H-1,2,4-triazol-3-ylthio)acetamido)-3-chlorobenzoic acid

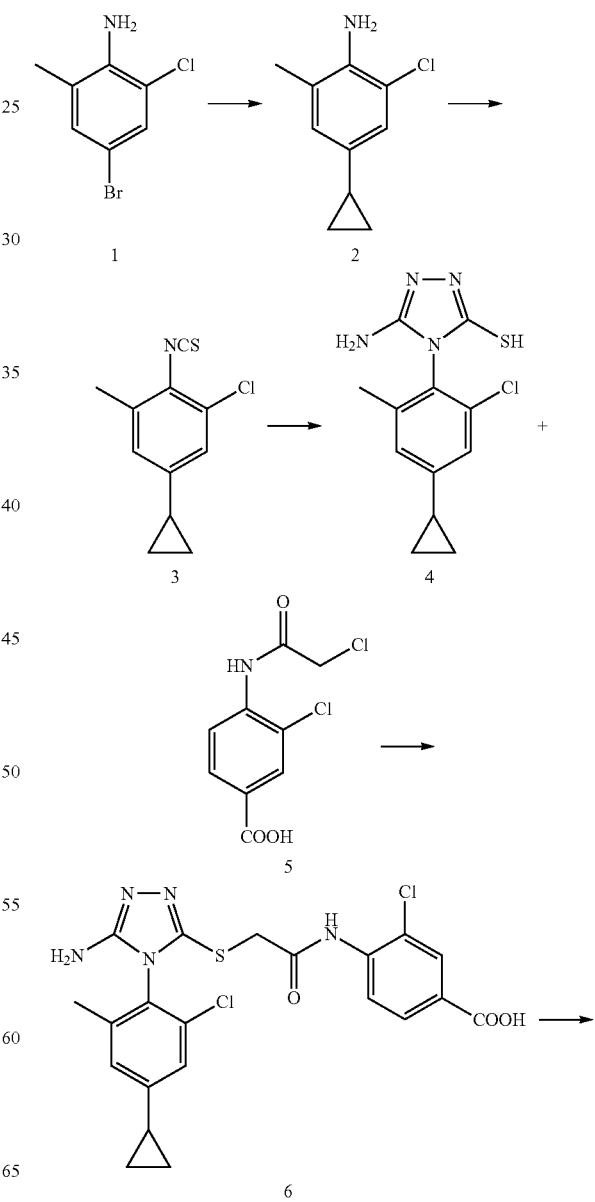

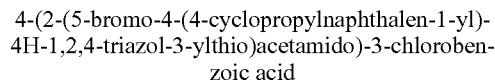

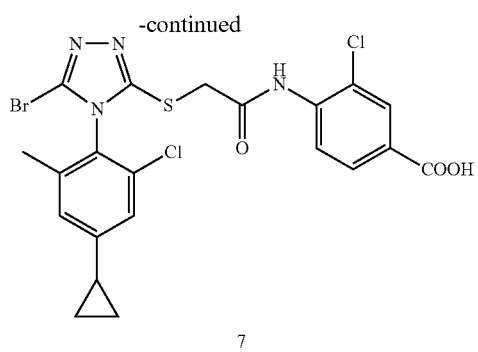

To a solution of 1 (1 g, 4.5 mmol), cyclopropyl boronic acid (506 mg, 5.9 mmol), potassium phosphate (3.34 g, 15.8 mmol) and tricyclohexylphosphine (126 mg, 0.45 mmol) in toluene (20 mL) and water (0.76 mL) under nitrogen atmosphere was added palladium acetate (51 mg, 0.23 mmol). The mixture was heated to 100° C. for 3 h and then cooled to room temperature. Water was added and the mixture extracted with ethyl acetate, dried over sodium sulfate and concentrated to give 775 mg of crude 2-chloro-4-cyclopropyl-6-methylbenzenamine (2) that was used in the next step without further purification.

Compound 2 (775 mg, 4.3 mmol) was dissolved in 9 mL of dichloromethane. Sodium bicarbonate (4.5 mL, sat. solution) and thiophosgene (0.33 mL, 4.3 mmol) were added and the mixture stirred at room temperature for 1 h. Then, the organic layer was separated, dried over sodium sulfate and concentrated to afford 935 mg of 1-chloro-5-cyclopropyl-2-isothiocyanato-3-methylbenzene (3) which was used in the next step without further purification.

Compound 3 (935 mg, 4.2 mmol) was dissolved in 5 mL of dimethylformamide, aminoguanidine hydrochloride salt (695 mg, 6.3 mmol) and diisopropyl ethylamine (1.1 mL, 6.3 mmol) were added and the mixture stirred at 50° C. for 18 hours. The mixture was then concentrated and to the resulting residue was added 2M aqueous sodium hydroxide solution (20 mL). The mixture was stirred at 50° C. for 18 hours and then cooled to room temperature. The resulting mixture was then neutralized with aqueous 1N HCl and the precipitate (product) collected to give 5-amino-4-(2-chloro-4-cyclopropyl-6-methylphenyl)-4H-1,2,4-triazole-3-thiol (4). (780 mg, 66% yield)

Compound 4 (100 mg, 0.36 mmol) and 3-chloro-4-(2-chloroacetamido)benzoic acid (5) (88 mg, 0.36 mmol) were dissolved in DMF (2 mL) and the mixture was stirred at 50° C. for 18 hours. Water was then added and the mixture extracted with ethyl acetate. The organic layer was separated, dried over sodium sulfate and concentrated to give 192 mg, of crude 4-(2-(5-amino-4-(2-chloro-4-cyclopropyl-6-methylphenyl)-4H-1,2,4-triazol-3-ylthio)acetamido)-3-chlorobenzoic acid (6) which was used in next step without further purification.

Dichloroacetic acid (0.065 mL, 0.78 mmol) was added to a mixture of compound 6 (192 mg, 0.39 mmol), benzyltriethyl ammonium bromide (318 mg, 1.17 mmol) and sodium nitrite (538 mg, 7.8 mmol) in dibromomethane (10 mL). The mixture was stirred at room temperature for 18 hours in the dark. The reaction mixture was then concentrated and the resulting residue was purified by prep. TLC (95% dichloromethane/5% methanol) to afford 88 mg, 42% yield of 4-(2-(5-bromo-4-(2-chloro-4-cyclopropyl-6-methylphenyl)-4H-1,2,4-triazol-3-ylthio)acetamido)-3-chlorobenzoic acid (7).

4-(2-(5-bromo-4-(4-cyclopropylnaphthalen-1-yl)-4H-1,2,4-triazol-3-ylthio)acetamido)-3-chlorobenzoic acid

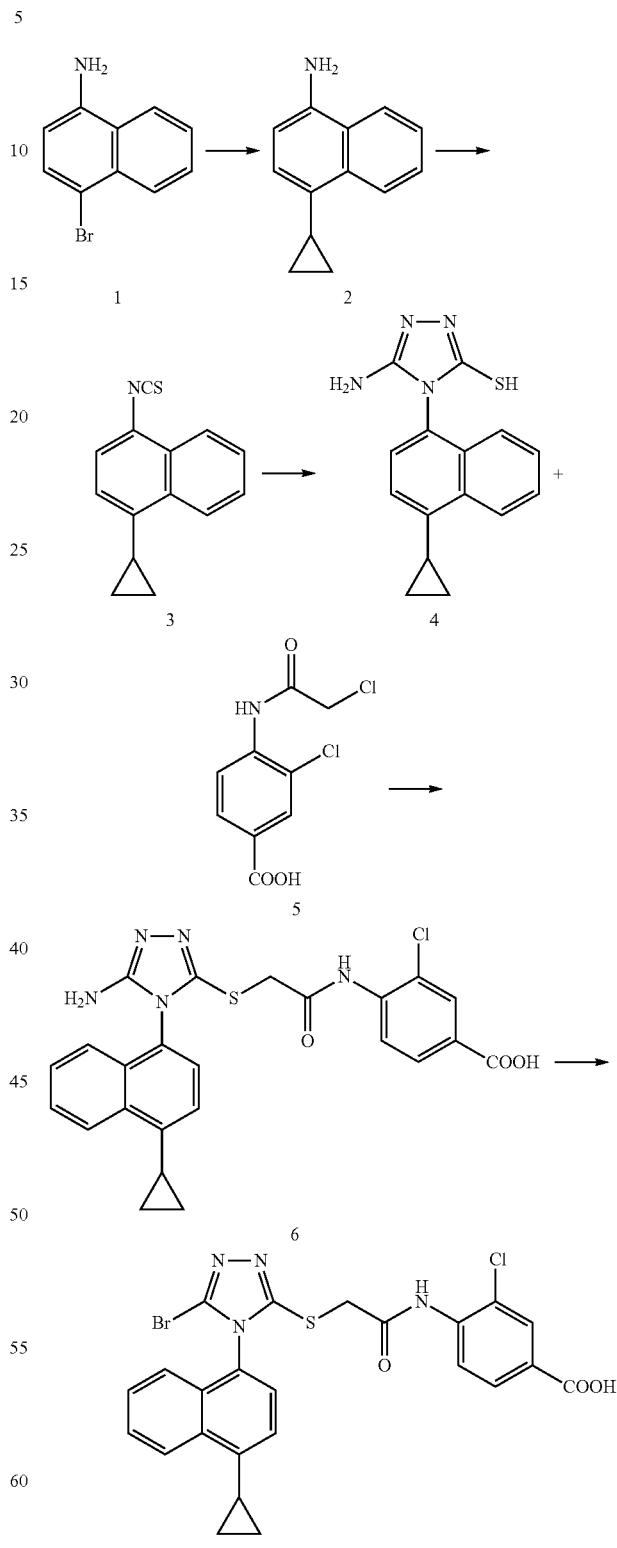

To a solution of 1 (500 mg, 2.01 mmol), cyclopropyl boronic acid (225 mg, 2.62 mmol), potassium phosphate (1.49 g, 7.04 mmol) and tricyclohexylphosphine (56 mg, 0.2 mmol) in toluene (10 mL) and water (0.4 mL) under nitrogen atmosphere was added palladium acetate (23 mg, 0.1 mmol). The mixture was heated to 100° C. for 3 h and then cooled to room temperature. Water was added and the mixture extracted with ethyl acetate, dried over sodium sulfate and concentrated to give 550 mg of crude 4-cyclopropylnaphthalen-1-amine (2) that was used in the next step without further purification.

Compound 2 (440 mg, 2.6 mmol) was dissolved in 14 mL of dichloromethane. Sodium bicarbonate (7 mL, sat. solution) and thiophosgene (0.2 mL, 2.6 mmol) were added and the mixture stirred at room temperature for 1 h. Then, the organic layer was separated, dried over sodium sulfate and concentrated to afford 877 mg, 99% yield of 1-cyclopropyl-4-isothiocyanatonaphthalene (3) which was used in the next step without further purification Compound 3 (447 mg, 2.1 mmol) was dissolved in 3 mL of dimethylformamide, aminoguanidine hydrochloride salt (355 mg, 3.2 mmol) and diisopropyl ethylamine (0.56 mL, 3.2 mmol) were added and the mixture stirred at 50° C. for 18 hours. The mixture was then concentrated and to the resulting residue was added 2M aqueous sodium hydroxide solution (10 mL). The mixture was stirred at 50° C. for 18 hours and then cooled to room temperature. The resulting mixture was then neutralized with aqueous 1N HCl and the precipitate (product) collected to give 5-amino-4-(4-cyclopropylnaphthalen-1-yl)-4H-1,2,4-triazole-3-thiol (4). (240 mg, 44% yield)

Compound 4 (789 mg, 2.79 mmol) and 3-chloro-4-(2-chloroacetamido)benzoic acid (5) (693 mg, 2.79 mmol) were dissolved in DMF (6 mL) and the mixture was stirred at 50° C. for 18 hours. Water was then added and the mixture extracted with ethyl acetate. The organic layer was separated, dried over sodium sulfate and concentrated to give 1.04 g, 75% yield of 4-(2-(5-amino-4-(4-cyclopropylnaphthalen-1-yl)-4H-1,2,4-triazol-3-ylthio)acetamido)-3-chlorobenzoic acid (6).

Dichloroacetic acid (0.35 mL, 4.2 mmol) was added to a mixture of compound 6 (1.04 g, 2.1 mmol), benzyltriethyl ammonium bromide (1.65 g, 6.1 mmol) and sodium nitrite (2.9 g, 42.1 mmol) in dibromomethane (44 mL). The mixture was stirred at room temperature for 18 hours in the dark. The reaction mixture was then concentrated and the resulting residue was purified by column chromatography (95% dichloromethane/5% methanol) to afford 393 mg, 34% yield of 4-(2-(5-bromo-4-(4-cyclopropylnaphthalen-1-yl)-4H-1,2,4-triazol-3-ylthio)acetamido)-3-chlorobenzoic acid (7).

4-(2-(5-bromo-4-(7-methoxy-4-methylnaphthalen-1-yl)-4H-1,2,4-triazol-3-ylthio)acetamido)-3-chlorobenzoic acid

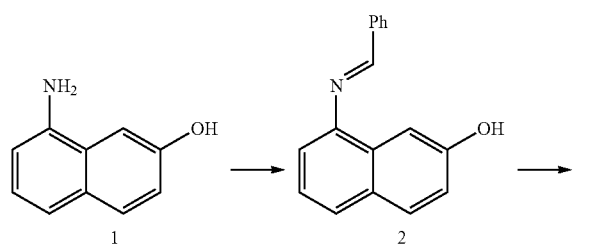

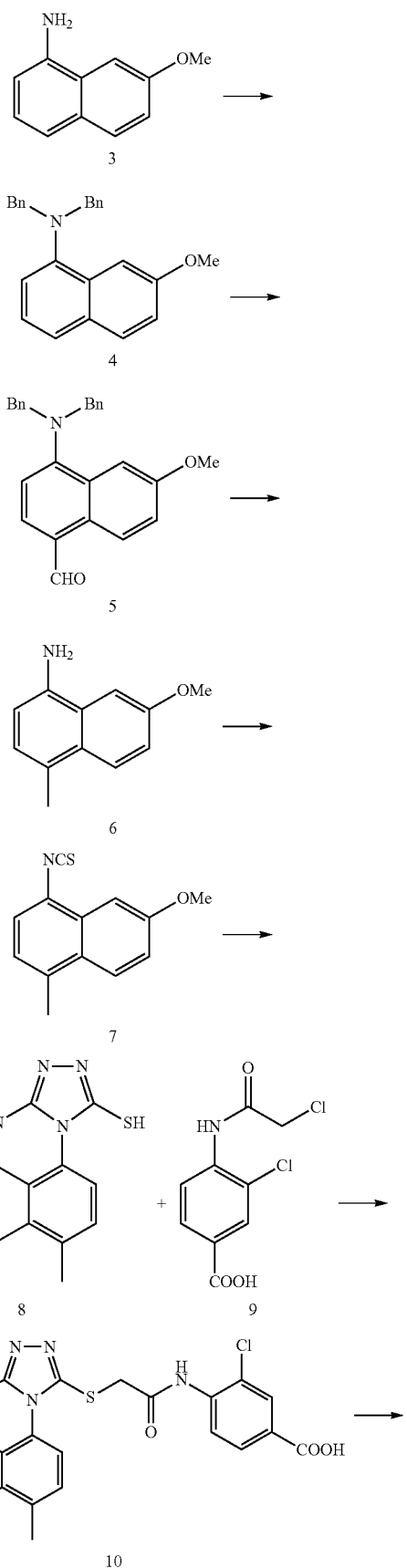

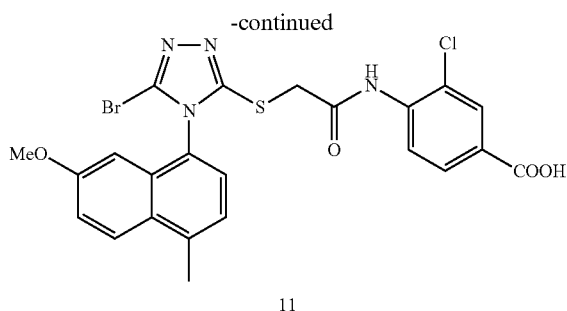

11

A mixture of 8-amino-2-naphthol 1 (8.2 g, 52 mmol), benzaldehyde (16 mL, 156 mmol) and sodium sulfate (41.3 g, 291 mmol) in THF (100 mL) was stirred at reflux over night. The mixture was cooled to room temperature, filtered and concentrated under reduced pressure. The resulting residue was purified by column chromatography (hexane/ethyl acetate/triethyl amine 75/23/2) to give 12.65 g of impure (E)-8-(benzylideneamino)naphthalen-2-ol (2) which was used in the next step without further purification.

A mixture of 2 (12.65 g, 51.2 mmol), MeI (6.4 mL, 102 mmol) and NaOH (6.14 g, 153 mmol) in acetone (125 mL) was stirred at room temperature for 2 hours. The resulting mixture was concentrated and the residue dissolved in ether, washed with water and brine and concentrated. The resulting residue was dissolved in 2N HCl-THF (780 mL, 2:1) and stirred at room temperature for 1.5 hrs. The resulting solution was washed with ether, the aqueous layer basified with Na2CO3 and extracted with ether. The organic layer was washed with brine, dried over sodium sulfate and concentrated. The resulting residue was purified by column chromatography (Hex/EtOAc 3:1) to give 6.94 g, 78% yield of 7-methoxynaphthalen-1-amine (3).

To a stirred mixture of 3 (6.94 g, 40 mmol) and potassium carbonate (16.6 g, 120 mmol) in acetone (100 mL) was added benzyl bromide (19.0 mL, 160 mmol) at 0° C. The mixture was refluxed for 3 days and cooled to room temperature. The precipitate removed and the filtrate concentrated. The resulting residue was purified by column chromatography (Hex 100%) to remove the unreacted benzyl bromide and then with ethyl acetate (100%) to give 11.75 g, 83% yield of N,N-dibenzyl-7-methoxynaphthalen-1-amine (4).

To a stirred solution of DMF (30 mL) was added POCl3 (10.65 mL, 116 mmol) over 30 minutes at 0° C. The mixture was then stirred at 0° C. for 30 minutes and added 4 (11.75 g, 33.2 mmol) in DMF (120 mL). The mixture was stirred at room temperature for six days and the poured into ice-water. The product mixture was extracted with dichloromethane and the organic layer washed with water, aqueous sodium bicarbonate and brine, dried over sodium sulfate and concentrated to afford 13.58 g of 4-(dibenzylamino)-6-methoxy-1-naphthaldehyde (5) which was used in next step without further purification.

A mixture of 5 (5.0 g, 13.1 mmol) and Pd/Carbon (812 mg) in methanol (150 mL) was stirred under hydrogen atmosphere (40 PSI) for 18 hours. The mixture was passed through celite and concentrated. The resulting residue was purified by column chromatography (Hex/EtOAC 3:1) to give 826 mg, 35% yield of 7-methoxy-4-methylnaphthalen-1-amine (6).

Compound 6 (826 mg, 4.4 mmol) was dissolved in 25 mL of dichloromethane. Sodium bicarbonate (15 mL, sat. solution) and thiophosgene (0.34 mL, 4.4 mmol) were added and the mixture stirred at room temperature for 1 h. Then, the organic layer was separated, dried over sodium sulfate and concentrated to afford 1.9 g, 99% yield of 4-isothiocyanato-6-methoxy-1-methylnaphthalene (7) which was used in the next step without further purification Compound 7 (1.0 g, 4.4 mmol) was dissolved in 10 mL of dimethylformamide, aminoguanidine hydrochloride salt (723 mg, 6.5 mmol) and diisopropyl ethylamine (1.14 mL, 6.5 mmol) were added and the mixture stirred at 50° C. for 18 hours. The mixture was then concentrated and to the resulting residue was added 2M aqueous sodium hydroxide solution (10 mL). The mixture was stirred at 50° C. for 18 hours and then cooled to room temperature. The resulting mixture was then neutralized with aqueous 1N HCl and the precipitate (product) collected to give 5-amino-4-(7-methoxy-4-methylnaphthalen-1-yl)-4H-1,2,4-triazole-3-thiol (8). (1.14 mg, 91% yield)

Compound 8 (200 mg, 0.7 mmol) and 3-chloro-4-(2-chloroacetamido)benzoic acid (9) (174 mg, 0.7 mmol) were dissolved in DMF (3 mL) and the mixture was stirred at 50° C. for 18 hours. Water was then added and the mixture extracted with ethyl acetate. The organic layer was separated, dried over sodium sulfate and concentrated to give 304 mg of 4-(2-(5-amino-4-(7-methoxy-4-methylnaphthalen-1-yl)-4H-1,2,4-triazol-3-ylthio)acetamido)-3-chlorobenzoic acid (10) which was used in the next step without further purification.

Dichloroacetic acid (0.1 mL, 1.2 mmol) was added to a mixture of compound 10 (304 mg, 0.6 mmol), benzyltriethyl ammonium bromide (492 mg, 1.8 mmol) and sodium nitrite (828 mg, 12 mmol) in dibromomethane (10 mL). The mixture was stirred at room temperature for 18 hours in the dark. The reaction mixture was then concentrated and the resulting residue was purified by column chromatography (95% dichloromethane/5% methanol) to afford 80 mg, 24% yield of 4-(2-(5-bromo-4-(7-methoxy-4-methylnaphthalen-1-yl)-4H-1,2,4-triazol-3-yltmo)acetamido)-3-chlorobenzoic acid (11).

2-[5-Bromo-4-(4-cyclopropylnaphthalen-1-yl)-4H-[1,2,4]triazol-3-ylsulfanyl]-N-(2-chloro-4-N-propionylsulfamoylphenyl)acetamide

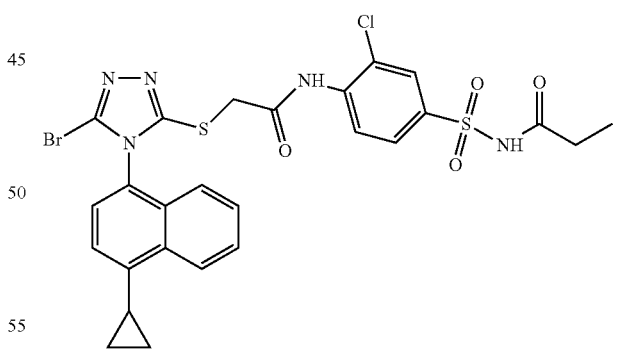

A 50 mL round-bottomed flask was charged with 2-[5-bromo-4-(4-cyclopropyl-naphthalen-1-yl)-4H-[1,2,4]triazol-3-ylsulfanyl]-N-(2-chloro-4-sulfamoylphenyl)-acetamide (45 mg, 0.076 mmol), EDC (29 mg, 0.15 mmol), and propionic acid (6.7 μL, 0.09 mmol) in the mixture of 5 mL THF and 5 mL methylene chloride. To the mixture was added DMAP (18.3 mg, 0.15 mmol) in one portion. The reaction mixture was stirred at RT for 14 h. The solvents were evaporated under reduced pressure yielding thick oily residue. The residue was redissolved in 20 mL methylene chloride, then it was washed with 20 mL 2.0 M aq. HCl solution. The organic layer was dried over Na2SO4. The solvent was removed by a rotavapor yielding oily residue. The residue was purified by silica-gel column chromatography with a mixture of methanol and methylene chloride (1:9). 18.5 mg (38%) of the desired product was obtained as white solids.

2-[5-Bromo-4-(4-cyclopropyl-naphthalen-1-yl)-4H-[1,2,4]triazol-3-ylsulfanyl]-N-(2-chloro-4-propionyl-sulfamoyl-phenyl)lysinamide

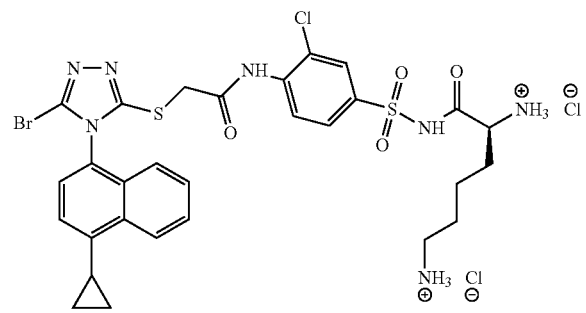 [SMILES: [NH3+]CCCC[C@H]([NH3+])C(=O)NS(=O)(=O)c1ccc(NC(=O)CSc2nnc(Br)n2-c2ccc(C3CC3)c3ccccc23)c(Cl)c1 ; [Cl-] ; [Cl-]]

A 25 mL round-bottomed flask was charged with 2-[5-bromo-4-(4-cyclopropyl-naphthalen-1-yl)-4H-[1,2,4]triazol-3-ylsulfanyl]-N-(2-chloro-4-sulfamoylphenyl)acetamide (50 mg, 0.085 mmol), EDC (35 mg, 0.18 mmol), Boc-Lys(Boc)-OH DCHA (47 mg, 0.09 mmol) in the mixture of 5 mL THF and 5 mL methylene chloride. To the mixture was added DMAP (16 mg, 0.13 mmol) in one portion. The reaction mixture was stirred at RT for 14 h. The solvents were evaporated under reduced pressure yielding thick oily residue. The residue was dissolved in 5 mL 4.0 M HCl in dioxane. The reaction was stirred at RT for 14 h. The solvent was evaporated under reduced pressure yielding thick oily residue. The residue was washed successively with 10 mL methylene chloride and 10 mL ether yielding the title compound as a light yellow solid (44 mg, 65%).

Reagents

1-Methyl-4-nitro-naphthalene

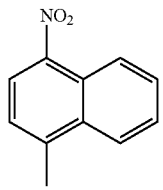

To 1-methylnaphthalene (8.0 g, 56 mmol) in round bottom flask at 0° C. was added nitric acid (26 mL) dropwise. (NOTE: A slow addition of nitric acid is most important to avoid the formation of the other regioisomers). After the reaction mixture was stirred for an additional 15 min at 0° C., it was poured into 65 mL of H$_2$O. The aqueous solution was extracted with benzene twice and the combined benzene solution was washed with 10% NaOH solution, dried with Na$_2$SO$_4$, and concentrated. Silica gel chromatography (EtOAc:Hexanes=5:95) gave product still containing a few percentage of the other regioisomer. It was recrystallized with EtOAc/Hexanes to give 9.0 g (43%) of 1.

4-Methyl-naphthalen-1-ylamine

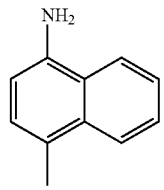

To a solution of 1-methyl-4-nitro-naphthyl-amine (4.0 g, 21 mmol) in ethanol (300 mL) was added Raney-Nickel (4 scoops). The mixture was stirred under H$_2$ (1 atm) for 16 h. The reaction was filtered through a pad of Celite and concentrated. Purification by silica gel flash column chromatography (EtOAc:Hexanes=15:85) provided product (3.2 g, 75%).

4-Ethyl-5,6,7,8-tetrahydro-naphthalen-1-ylamine

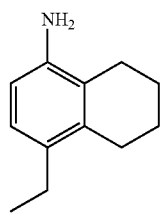

The procedure was essentially identical to the route for 4-Methyl-naphthalen-1-ylamine as described above, however, started with a solution of 5-ethyl-8-nitro-1,2,3,4-tetrahydro-naphthalene (795 mg, 3.95 mmol).

4-Methyl-naphthalen-1-yl-thiosemicarbazide

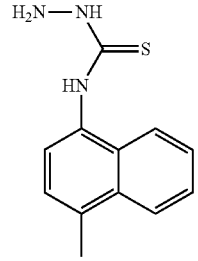 [SMILES: Cc1ccc(NC(=S)NN)c2ccccc12]

To a solution of thiophosgene (0.33 mL, 4.3 mmol) in anhydrous methylene chloride (5 mL) at 0° C. was added dropwise a solution of 4-methyl naphthyl amine (671 mg, 4.3 mmol) and diisopropylethyl amine (1.5 mL, 8.6 mmol) in anhydrous methylene chloride (5 mL). After the reaction mixture was stirred for an additional 10 min at 0° C., it was washed with 1% HCl solution and then H$_2$O, dried with Na$_2$SO$_4$, and concentrated to give dark brown oil. The oil was dissolved in hexanes (15 mL) and the resulting brown slurry was filtered. The filtrated was concentrated to give a pure thioisocyanate. To a solution of the thioisocyanate in anhydrous acetonitrile (20 mL) was added hydrazine (0.13 mL, 4.3 mmol) at RT. After stirring at RT for 20 min, the mixture was concentrated. The resulting yellow oil was triturated with EtOAc:Hexanes (1:1) to give (701 mg, 71% yield) of product as an off-white solid.

5-Difluoromethyl-4-(4-methyl-naphthalen-1-yl)-4H-[1,2,4]trizole-3-thiol

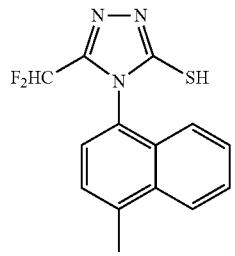 [SMILES: Cc1ccc(-n2c(S)nnc2C(F)F)c2ccccc12]

A solution of 4-methyl naphthyl thiosemicarbazide (180 mg, 0.78 mmol) in difluoroacetic acid (2 mL) was heated at 100° C. for 4 h. When the mixture was cooled to room temperature, white solid crystallized out of reaction mixture. To collect more products, 2 mL of hexanes was added to the mixture. Filtration gave (179 mg, 79% yield) product as a white solid.

5-Fluoromethyl-4-(4-methyl-naphthalen-1-yl-4H-[1,2,4]trizole-3-thiol

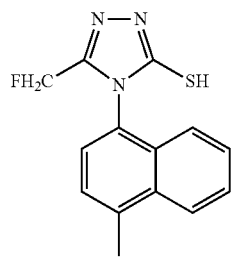

To a solution of 4-methyl-naphthlyl-thiosemicarbazide (158 mg, 0.68 mmol) in MeOH (10 mL) and 4.37 M NaOMe (0.23 mL, 1.02 mmol) was added ethyl fluoroacetate (0.13 mL, 1.37 mmol) and stirred at room temperature for 17 h. The reaction mixture was concentrated, added water and washed with diethyl ether. To the aqueous layer, the pH was adjusted with HCl and filtered off product as white solid in (78 mg, 42% yield). $^1$H NMR (DMSO, 300 MHz) δ 14.26 (s, 1H), 8.14 (d, J=8.4 Hz, 1H), 7.67-7.52 (m, 4H), 7.26 (d, J=8.4 Hz, 1H), 5.20 (dd, J=12.0, 21.0 Hz, 1H), 5.03 (dd, J=12.0, 20.4 Hz5 1H), 2.74 (s, 3H).

2-[5-Difluoromethyl-4-(4-methyl-naphthalen-1-yl)-4H-[1,2,4]triazol-3-ylsulfanyl]-N-(2-methyl-4-sulfamoyl-phenyl)-acetamide

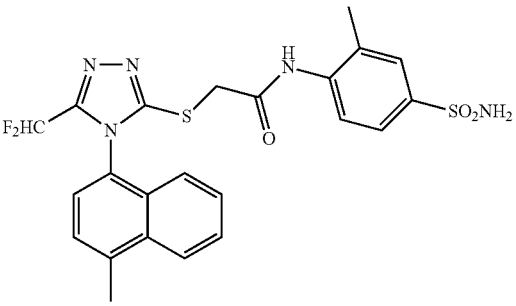 [SMILES: Cc1cc(S(N)(=O)=O)ccc1NC(=O)CSc1nnc(C(F)F)n1-c1ccc(C)c2ccccc12]

In a solution of 5-difluoromethyl-4-(4-methyl-naphthalen-1-yl)-4H-[1,2,4]triazole-3-thiol (53 mg, 0.18 mmol), K$_2$CO$_3$ (27.0 mg, 0.20 mmol) in DMF (1.5 mL) was added 2-methyl-N-(2-methyl-4-sulfamoyl-phenyl)-acetamide (47 mg, 0.18 mmol). The reaction mixture was stirred at room temperature for 16 h. Upon the completion of the reaction, H$_2$O (4.0 mL) was added to the reaction and stirred until precipitation occurred and filtered off product (77.0 mg, 83% yield). $^1$H NMR (DMSO, 300 MHz) δ 9.84 (broad s, 1H), 8.18 (d, J=8.0 Hz, 1H), 7.70-7.53 (m, 7H), 7.18 (t, J=51.5 Hz, 1H), 7.11 (d, J=8.0 Hz, 1H), 4.26 (s, 2H), 2.82 (s, 3H), 2.27 (s, 3H).

N-(2-Chloro-4-sulfamoyl-phenyl)-2-[5-difluoromethyl-4-(4-ethyl-5,6,7,8-tetrahydro-naphthalen-1-yl)-4H-[1,2,4]triazol-3-ylsulfanyl]-acetamide

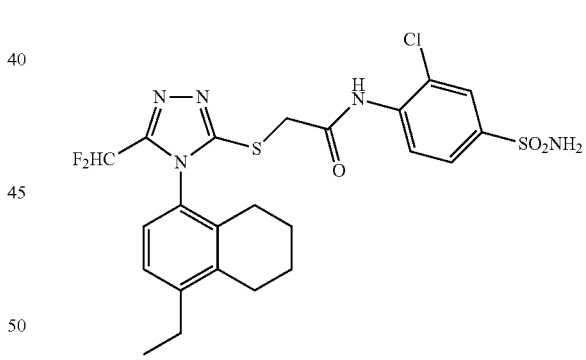

In a solution of 5-difluoromethyl-4-(4-ethyl-5,6,7,8-tetrahydro-naphthalen-1-yl)-4H-[1,2,4]triazole-3-thiol (85 mg, 0.28 mmol), K$_2$CO$_3$ (41.8 mg, 0.30 mmol) in DMF (2.0 mL) was added 2-chloro-N-(2-methyl-4-sulfamoyl-phenyl)-acetamide (77.8 mg, 0.28 mmol). The reaction mixture was stirred at room temperature overnight. Upon completion of the reaction, MeOH was added to the reaction and stirred until precipitation occurred and filtered off product (71.0 mg, 46% yield). $^1$H NMR (DMSO, 300 MHz) δ 10.14 (s, 1H), 8.03 (d, J=8.1 Hz, 1H), 7.88 (d, J=2.4 Hz, 1H), 7.74 (dd, J=2.1, 8.4 Hz, 1H), 7.46 (broad s, 2H), 7.34-7.00 (m, 3H), 4.33 (apparent q, J=15.6 Hz, 2H), 2.71 (t, J=5.7 Hz, 2H), 2.62 (q, J=7.5 Hz, 2H), 2.28-2.08 (m, 2H), 1.72-1.60 (m, 4H), 1.19 (t, J=7.5 Hz, 3H).

41

N-(2-Chloro-4-sulfamoyl-phenyl)-2-[5-difluoromethyl-4-(4-methyl-naphthalen-1-yl)-4H-[1,2,4]triazol-3-ylsulfanyl]-acetamide

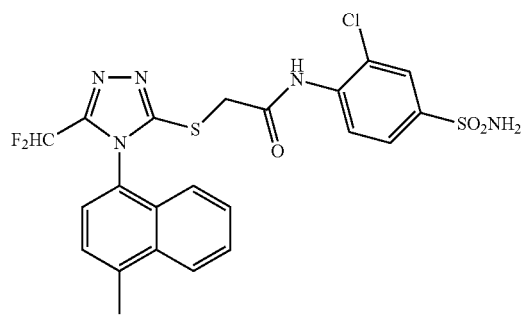 [SMILES: Cc1ccc(-n2c(SCC(=O)Nc3ccc(S(N)(=O)=O)cc3Cl)nnc2C(F)F)c2ccccc12]

In a solution of 5-difluoromethyl-4-(4-methyl-naphthalen-1-yl)-4H-[1,2,4]triazole-3-thiol (59 mg, 0.20 mmol), K₂CO₃ (30.0 mg, 0.22 mmol) in DMF (1.5 mL) was added 2-chloro-N-(2-methyl-4-sulfamoyl-phenyl)-acetamide (57 mg, 0.20 mmol). The reaction mixture was stirred at room temperature for 16 h. Upon the completion of the reaction, H2O (4.0 mL) was added to the reaction and stirred until precipitation occurred and filtered off product (77.0 mg, 71% yield). $^1$H NMR (DMSO, 300 MHz) δ 10.11 (broad s, 1H), 8.18 (d, J=10.0 Hz, 1H), 8.01 (d, J=10.0 Hz, 1H), 7.87 (s, 1H), 7.75-7.54 (m, 5H), 7.46 (broad s, 2H), 7.18 (t, J=50.0 Hz, 1H), 7.11 (d, J=10.0 Hz, 1H), 4.32 (s, 2H), 2.27 (s, 3H).

2-[5-Fluoromethyl-4-(4-methyl-naphthalen-1-yl)-4H-[1,2,4]triazol-3-ylsulfanyl]-N-(2-methyl-4-sulfamoyl-phenyl)-acetamide

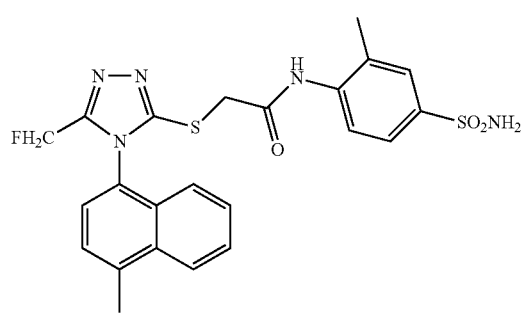

In a solution of 5-fluoromethyl-4-(4-methyl-naphthalen-1-yl)-4H-[1,2,4]triazole-3-thiol (89 mg, 0.33 mmol), K₂CO₃ (50.0 mg, 0.36 mmol) in DMF (2.0 mL) was added 2-chloro-N-(2-methyl-4-sulfamoyl-phenyl)-acetamide (87 mg, 0.33 mmol). The reaction mixture was stirred at room temperature for 16 h. Upon the completion of the reaction, H₂O (2.0 mL) was added to the reaction and stirred til precipitation occurred and filtered. Purified by reverse phase HPLC resulted product as a solid in (53.3 mg, 50% yield). $^1$H NMR (DMSO, 300 MHz) δ 9.84 (broad s, 1H), 8.18 (d, J=8.4 Hz, 1H), 7.71-7.53 (m, 7H), 7.26 (s, 2H), 7.10 (d, J=8.7 Hz, 1H), 5.34 (dd, J=12.0, 27.3 Hz, 1H), 5.18 (dd, J=12.3, 26.4 Hz, 1H), 4.22 (s, 2H), 2.75 (s, 3H), 2.25 (s, 3H).

42

N-(2-Chloro-4-sulfamoyl-phenyl)-2-[5-fluoromethyl-4-(4-methyl-naphthalen-1-yl)-4H-[1,2,4]triazol-3-ylsulfanyl]-acetamide

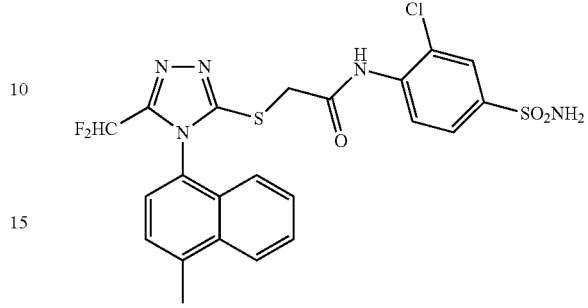

In a solution of 5-fluoromethyl-4-(4-methyl-naphthalen-1-yl)-4H-[1,2,4]triazole-3-thiol (89 mg, 0.33 mmol), K₂CO₃ (50.0 mg, 0.36 mmol) in DMF (2.0 mL) was added 2-chloro-N-(2-chloro-4-sulfamoyl-phenyl)-acetamide (93 mg, 0.33 mmol). The reaction mixture was stirred at room temperature for 16 h. Upon the completion of the reaction, H₂O (2.0 mL) was added to the reaction and stirred til precipitation occurred and filtered to give solid (126.8 mg, 74% yield). $^1$H NMR (DMSO, 300 MHz) δ 10.12 (broad s, 1H), 8.18 (d, J=8.7 Hz, 1H), 8.04 (dd, J=4.8, 8.7 Hz), 7.87 (s, 1H), 7.76-7.52 (m, 5H), 7.46 (s, 2H), 7.11 (d, J=8.7 Hz, 1H), 5.35 (dd, J=12.3, 26.7 Hz, 1H), 5.19 (dd, J=11.7, 25.8 Hz, 1H), 4.26 (s, 2H), 2.75 (s, 3H).

N-(2-Chloro-4-sulfamoyl-phenyl)-2-[4-(4-ethyl-5,6,7,8-tetrahydro-naphthalen-1-yl)-5-fluoromethyl-4H-[1,2,4]triazol-3-ylsulfanyl]-acetamide

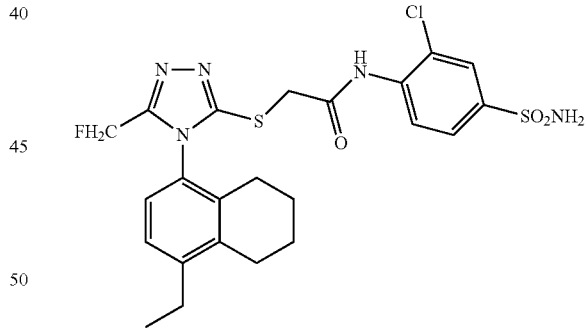

In a solution of 4-(4-ethyl-5,6,7,8-tetrahydro-naphthalen-1-yl)-5-fluoromethyl-4H-[1,2,4]triazole-3-thiol (85 mg, 0.29 mmol), K₂CO₃ (44.4 mg, 0.32 mmol) in DMF (2.0 mL) was added 2-chloro-N-(2-chloro-4-sulfamoyl-phenyl)-acetamide (82.6 mg, 0.29 mmol). The reaction mixture was stirred at room temperature for 16 h. Upon the completion of the reaction, H₂O (2.0 mL) was added to the reaction and stirred til precipitation occurred and filtered to give solid (73.0 mg, 47% yield).

1H NMR (ΔMΣO, 300 MHO δ 10.15 (s, 1H), 8.05 (d, J=8.4 Hz, 1H), 7.87 (s, 1H), 7.74 (d, J=8.4 Hz, 1H), 7.46 (s, 2H), 7.21-7.06 (m, 2H), 5.26 (d, J=48.0 Hz. 2H), 4.29 (apparent q, J=15.6 Hz, 2H), 2.71-2.58 (m, 3H), 2.25 (s, 1H), 2.25-2.09 (m, 2H), 1.72-1.59 (m, 4H), 1.19 (t, J=7.5 Hz, 3H).

Using the appropriate starting materials, the following compounds are prepared by procedures analogous to the methods disclosed above:

2-[5-Bromo-4-(2-chloro-4-(cyclopropylmethyl)phenyl)-4H-[1,2,4]-triazole-3-ylsulfanyl]-N-(2-chloro-4-sulfamoylphenyl)acetamide 2-[5-Bromo-4-(2-chloro-4-cyclobutylphenyl)-4H-[1,2,4]-triazole-3-ylsulfanyl]-N-(2-chloro-4-sulfamoylphenyl)acetamide 2-[5-Bromo-4-(2-chloro-4-(cyclopropylmethyl)naphthalen-1-yl)-4H-[1,2,4]-triazole-3-ylsulfanyl]-N-(2-chloro-4-sulfamoylphenyl)acetamide 2-[5-Bromo-4-(2-chloro-4-cyclopropylphenyl)-4H-[1,2,4]-triazole-3-ylsulfanyl]-N-(2-chloro-4-sulfamoylphenyl)acetamide 2-[5-Trifluoromethyl-4-(2-chloro-4-cyclopropylnaphthalen-1-yl)-4H-[1,2,4]-triazole-3-ylsulfanyl]-N-(2-chloro-4-sulfamoylphenyl)acetamide 2-[5-Bromo-4-(4-cyclopropyl-5,6,7,8-tetrahydronaphthalen-1-yl)-4H-[1,2,4]-triazole-3-ylsulfanyl]-N-(2-chloro-4-sulfamoylphenyl)acetamide 2-[5-Bromo-4-(4-ethylnaphthalen-1-yl)-4H-[1,2,4]-triazole-3-ylsulfanyl]-N-(2-chloro-4-sulfamoylphenyl)acetamide 2-[5-Bromo-4-(4-ethyl-5,6,7,8-tetrahydronaphthalen-1-yl)-4H-[1,2,4]-triazole-3-ylsulfanyl]-N-(2-chloro-4-sulfamoylphenyl)acetamide 2-[5-Bromo-4-(5-cyclopropylquinolin-8-yl)-4H-[1,2,4]-triazole-3-ylsulfanyl]-N-(2-chloro-4-sulfamoylphenyl)acetamide 2-[5-Bromo-4-(5-cyclopropylisoquinolin-8-yl)-4H-[1,2,4]-triazole-3-ylsulfanyl]-N-(2-chloro-4-sulfamoylphenyl)acetamide 2-[5-Bromo-4-(5-cyclopropylcinnolin-8-yl)-4H-[1,2,4]-triazole-3-ylsulfanyl]-N-(2-chloro-4-sulfamoylphenyl)acetamide 2-[5-Bromo-4-(1-methylacenaphthene-5-yl)-4H-[1,2,4]-triazole-3-ylsulfanyl]-N-(2-chloro-4-sulfamoylphenyl)acetamide 2-[5-Bromo-4-(2-methylacenaphthene-5-yl)-4H-[1,2,4]-triazole-3-ylsulfanyl]-N-(2-chloro-4-sulfamoylphenyl)acetamide 2-[5-Bromo-4-(1,1-dimethylacenaphthene-5-yl)-4H-[1,2,4]-triazole-3-ylsulfanyl]-N-(2-chloro-4-sulfamoylphenyl)acetamide Inhibition of HIV-1 Reverse Transcriptase Compounds were screened for inhibitory activity against human immunodeficiency virus type 1 (HIV-1) using a high throughput cell-based assay using HIV-1 expressing firefly luciferase as a reporter gene and pseudotyped with vesicular stomatitis virus envelope glycoprotein (VSV-G). Experimental procedures were essentially as described by Connor et al. in *Journal of Virology* (1996), 70: 5306-5311 (Characterization of the functional properties of env genes from long-term survivors of human immunodeficiency virus type 1 infection), and Popik et al. in *Journal of Virology* (2002), 76: 4709-4722 (Human immunodeficiency virus type 1 uses lipid raft-colocalized CD4 and chemokine receptors for productive entry into CD4+ T cells). It should be particularly appreciated that the virus contains two introduced mutations in the RT gene (K103N and Y181C, created by PCR mutagenesis) that render the virus highly resistant to current non-nucleoside HIV-1 drugs. Virus stocks were generated by cotransfection of plasmid DNA encoding VSV-G with vector pNL4-3Env(−)Luc(+) into 293T cells. Sixty-four hours after transfection, virus-containing medium was collected by centrifugation and stored frozen at −80° C.

HeLa cells were infected with the VSV-G pseudotyped virus in the presence of screening compounds in a 384-well microtiter plate format. Forty-eight hours after initial infection, lysis buffer and Luciferase Assay Reagent (Promega) was added to the cells and luciferase activity was determined by counting the resultant luminescence using a LJL luminometer. Since the luciferase gene is carried in the virus genome, its expression level directly reflects the virus replication level in the presence of a compound.

To evaluate the activity of the compounds against wild type HIV-1, a HeLa-JC53 cell line that expresses high levels of CD4 and CCR5 was employed (Platt et al., *Journal of Virology* (1998), 72: 2855-2864: Effect of CCR5 and CD4 cell surface concentrations on infection by macrophagetropic isolates of human immunodeficiency virus type 1). The cell line was modified by isolation of a stable cell line that expresses luciferase under the control of the HIV-1 promoter (long terminal repeat, i.e., LTR). HIV-1 infection of this cell line stimulates the transcription of luciferase from the HIV-1 promoter and the luciferase gene expression level is proportional to the level of virus replication (Harrington et al. in *Journal of Virology* Methods (2000), 88: 111-115: Direct detection of infection of HIV-1 in blood using a centrifugation-indicator cell assay; and Roos et al. in *Virology* (2000), 273: 307-315: LuSIV cells: a reporter cell line for the detection and quantitation of a single cycle of HIV and SIV replication). Procedures for virus infection, compound testing and luciferase activity determination were the same as for the VSV-G pseudotyped HIV-1.

Two approaches were used to evaluate the cytotoxicity of the positive compounds discovered in the HIV-1 virus assays. The first approach employed another modified HeLa-JC53 cell line that constitutively expresses high level of luciferase without virus infection. The level of luciferase expression in these cells served as an indicator for cell replication in the presence of the compounds. Procedures for compound testing and luciferase activity determination were the same as for the virus infection tests. The other toxicity assay utilized HeLa-JC53 cells and a commercially available MTS assay kit (Promega) that measures the mitochondria function of the cells.

Using similar methods as described above, 2-[5-bromo-4-(4-cyclopropylnaphthalen-1-yl)-4H-[1,2,4]triazol-3-ylsulfanyl]-N-(2-methyl-4-sulfamoylphenyl)acetamide and 2-[5-bromo-4-(4-ethylnaphthalen-1-yl)-4H-[1,2,4]triazol-3-ylsulfanyl]-N-(2-chloro-4-sulfamoylphenyl)-acetamide were synthesized, as were the N-4-carbamyl analog, 2-[5-bromo-4-(4-ethyl-naphthalen-1-yl)-4H-[1,2,4]triazol-3-ylsulfanyl]-N-(2-chloro-4-carbamoylphenyl)-acetamide and the N-4-carboxyl analog. Each of the compounds was tested against a panel of mutant HIV reverse transcriptases, including 20 of the 22 of the mutants that are found in about 2% or more of the patient samples that are resistant to the most widely used non-nucleoside HIV-RT inhibitor efavirenz ((4S)-6-chloro-4-(cyclopropylethynyl)-1,4-dihydro-4-(trifluoromethyl)-2H-3,1-benzoxazin-2-one). For each of the 20 high-prevalence mutants tested, at least one of these compounds was more than 20 fold more potent than efavirenz or showed $EC_{50}$ of less than 1 nM. In most cases both criteria were met. In the majority of cases all three compounds were more potent than efavirenz. Compounds were compared for activity on wild type, Y181C and Y188L mutant reverse transcriptases. Both amides were significantly superior to the carboxylic acid on all three enzymes.

Results

Compounds of the invention were tested against the wild-type and four mutant HIV reverse transcriptases. The results are listed in Table 1 as $EC_{50}$ (nM) and $IC_{50}$ (nM). In the Table, A represents <50 nM, B is between 50 and 100 nM, and C is >100 nM. ND is not determined. Preferred compounds in this invention are those that exhibit activities on wild-type (WT) and resistant mutants below 50 nM in both $EC_{50}$ and $IC_{50}$.

TABLE 1

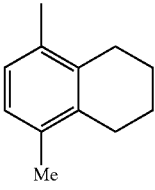

| No. | $R^1$ | A | Ar | $R_2$ | $EC_{50}$ WT (nM) | $EC_{50}$ Y181C (nM) | $EC_{50}$ Y188L (nM) | $IC_{50}$ WT RT (nM) | $IC_{50}$ Y181C (nM) | $IC_{50}$ Y188L (nM) |
|---|---|---|---|---|---|---|---|---|---|---|
| 1 | $CF_2H$ | 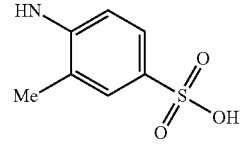 | 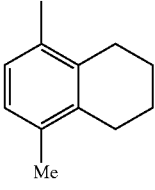 | H | C | C | C | A | C | C |
| 2 | $CF_2H$ | 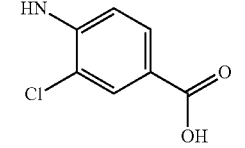 | 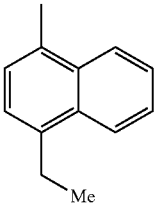 | H | A | A | A | A | A | C |
| 3 | $CF_2H$ | 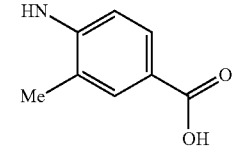 | 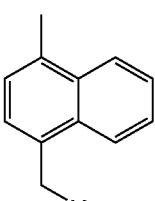 | H | A | B | C | A | C | C |
| 4 | $CF_2H$ | 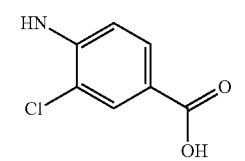 | 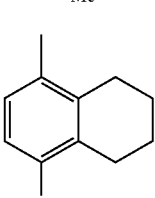 | H | A | A | A | A | A | C |
| 5 | $CF_2H$ | 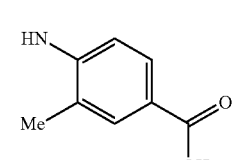 | 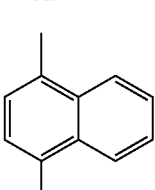 | H | A | C | C | A | C | C |
| 6 | Br | 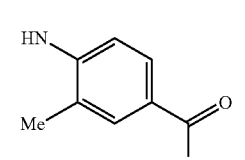 | | H | A | A | C | A | B | C |

TABLE 1-continued
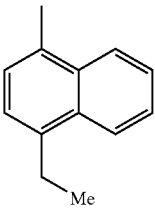
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 7 | Br | 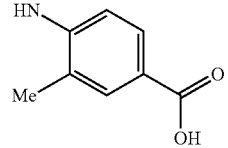 | 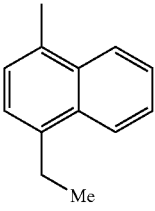 | H | | | | | | |
| 8 | Br | 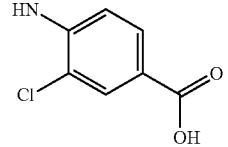 | 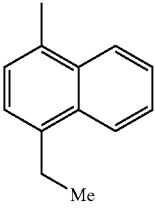 | H | A | A | A | A | A | C |
| 9 | Br | 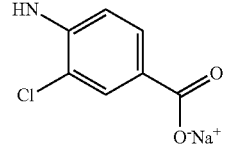 | 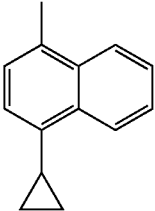 | H | A | A | A | | | |
| 10 | Br | 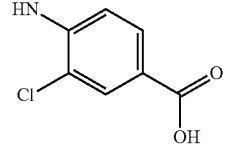 | 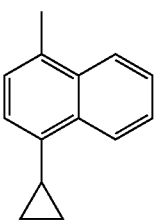 | H | A | A | A | A | A | C |
| 11 | Br | 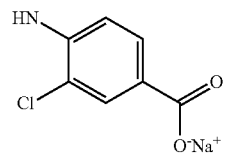 | 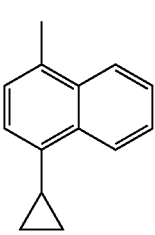 | H | A | A | A | A | A | B |
| 12 | Br | 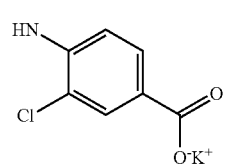 | | H | A | A | A | A | A | B |

TABLE 1-continued
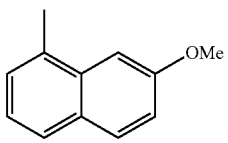
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 13 | Br | 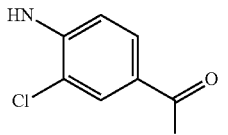 | 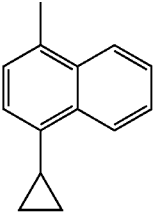 | H | A | A | A | A | A | C |
| 14 | CF₂H | 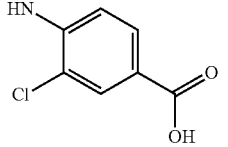 | 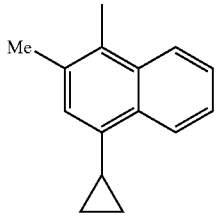 | H | A | A | A | A | A | C |
| 15 | Br | 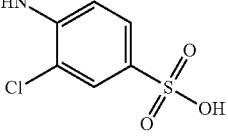 | 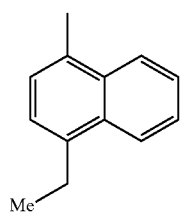 | H | A | B | C | A | A | B |
| 16 | CF₃ | 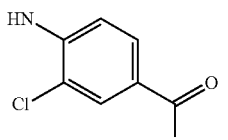 | 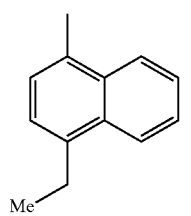 | H | A | B | C | A | A | C |
| 17 | CH₂F | 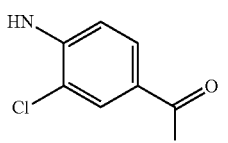 | 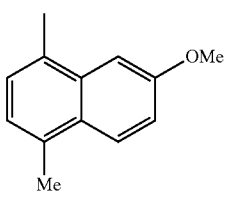 | H | A | A | C | A | A | C |
| 18 | Br | 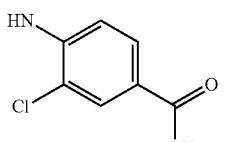 | | H | A | A | A | A | A | A |

TABLE 1-continued
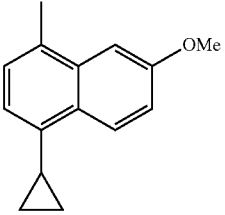 [SMILES: COc1ccc2c(C3CC3)ccc(C)c2c1]
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 19 | Br | 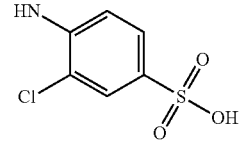 | 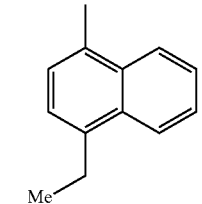 | H | B | B | C | A | A | B |
| 20 | Br | 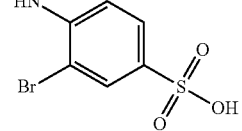 | 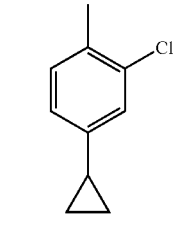 | H | C | C | C | A | A | B |
| 21 | Br | 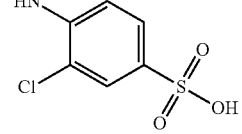 | 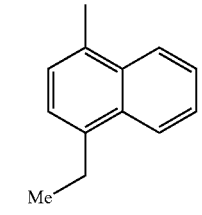 | H | B | C | C | A | A | C |
| 22 | Br | 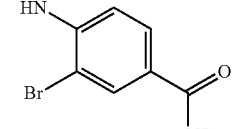 | 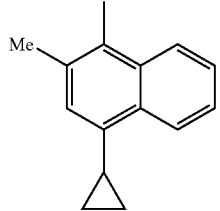 | H | A | A | B | A | A | B |
| 23 | Br | 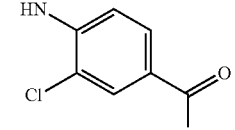 | 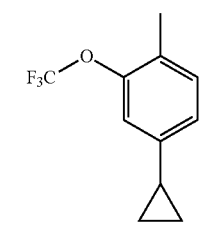 | H | A | A | A | A | A | C |
| 24 | Br | 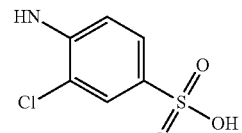 | | H | C | C | C | A | B | C |

TABLE 1-continued

| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 25 | Br | 3-Cl-4-Me-1-cyclobutyl-naphthalene | 3-Cl-4-(NH)-benzoic acid | H | A | A | A | A | A | B |
| 26 | Br | 4-Me-1-cyclobutyl-naphthalene | 3-Cl-4-(NH)-benzoic acid | H | A | A | A | A | A | C |
| 27 | Br | 5-Me-8-OMe-naphthalene | 3-Cl-4-(NH)-benzoic acid | H | A | A | C | A | B | C |
| 28 | Br | 3-Me-4-Cl-5-cyclopropyl-phenyl (Me, Cl, cyclopropyl) | 3-Cl-4-(NH)-benzoic acid | H | A | A | A | A | A | C |
| 29 | Br | 2-Et-4-Me-5-cyclopropyl-phenyl | 3-Cl-4-(NH)-benzoic acid | H | A | A | C | A | B | C |
| 30 | Br | 2-CF₃-4-Me-5-cyclopropyl-phenyl | 3-Cl-4-(NH)-benzoic acid | H | A | A | C | A | B | C |

TABLE 1-continued

| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 31 | Br | 2-chloro-4-cyclopropyl-toluene | 3-chloro-4-amino-benzoic acid | H | A | A | C | A | A | C |
| 32 | Br | 5-methyl-1-(cyclopropylmethoxy)naphthalene | 3-chloro-4-amino-benzoic acid | H | C | C | C | C | C | C |
| 33 | Br | 3,5-dimethyl-4-methyl-cyclopropylbenzene | 3-chloro-4-amino-benzoic acid | H | A | A | C | A | A | C |
| 34 | Br | 8-methyl-5-cyclopropyl-2-methoxynaphthalene | 3-chloro-4-amino-benzoic acid | H | A | A | A | | | |
| 35 | Br | 4-methyl-1-cyclopropyl-naphthalene | 3-methyl-4-amino-benzoic acid | H | A | | | A | | |
| 36 | CF₂H | 5-methyl-acenaphthylene | 3-chloro-4-amino-benzenesulfonamide | H | A | A | A | A | A | C |

TABLE 1-continued

| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 37 | Br | 5-methylacenaphthylene | 4-NH-3-Cl-benzenesulfonamide | H | A | A | A | A | A | B |
| 38 | Br | 5-methylacenaphthylene | 4-NH-3-Me-benzenesulfonamide | H | A | A | A | A | A | C |
| 39 | Br | 4-methyl-1-cyclopropylnaphthalene | 4-NH-3-Cl-benzenesulfonamide | H | A | A | A | A | A | B |
| 40 | Br | 4-methyl-1-cyclopropylnaphthalene | 4-NH-3-Me-benzenesulfonamide | H | A | A | A | A | A | C |
| 41 | CH₃ | 5-methyl-8-ethyl-tetrahydronaphthalene | 4-NH-3-Me-benzenesulfonamide | H | A | A | C | A | C | C |
| 42 | Br | 5-methyl-8-cyclopropylnaphthalene | 4-NH-3-Cl-benzenesulfonamide | H | A | A | A | A | A | C |

TABLE 1-continued
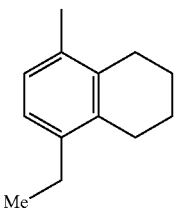
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 43 | CH₃ | 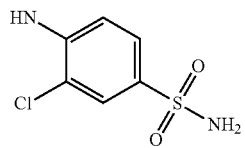 | 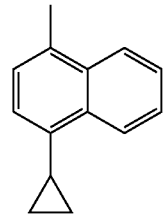 | H | A | A | A | A | B | C |
| 44 | CF₂H | 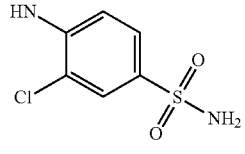 | 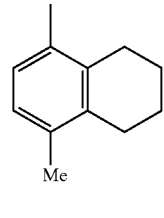 | H | A | A | A | A | A | C |
| 45 | CH₃ | 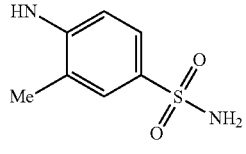 | 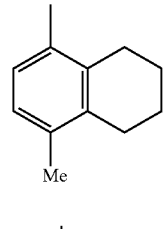 | H | A | A | B | A | C | C |
| 46 | CH₃ | 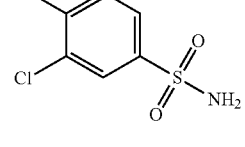 | 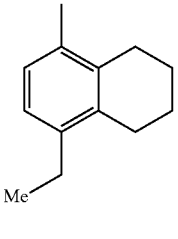 | H | A | A | A | A | B | C |
| 47 | CF₂H | 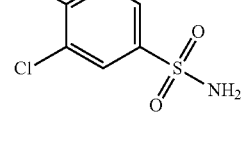 | 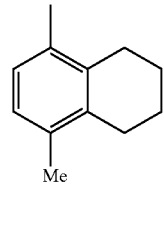 | H | A | A | A | A | A | C |
| 48 | CF₂H | 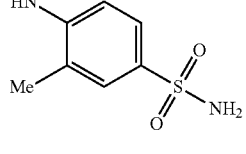 | | H | A | A | B | A | A | C |

TABLE 1-continued
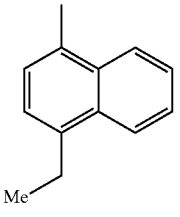
| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 49 | CFH$_2$ | 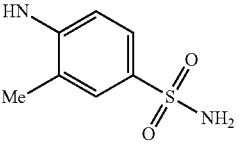 | 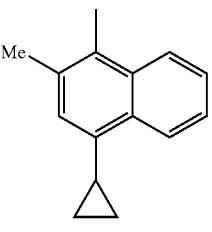 | H | A | A | C | A | B | C |
| 50 | Br | 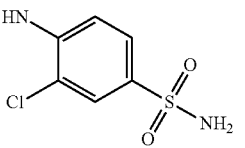 | 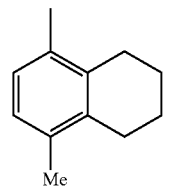 | H | A | A | A | A | A | B |
| 51 | CF$_2$H | 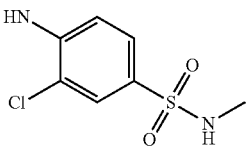 | 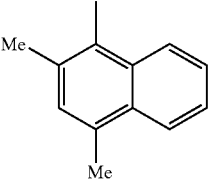 | H | A | A | A | A | A | C |
| 52 | CFH$_2$ | 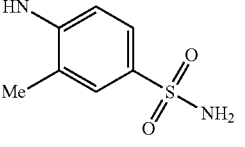 | 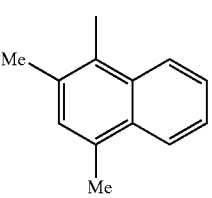 | H | A | A | A | A | C | C |
| 53 | CFH$_2$ | 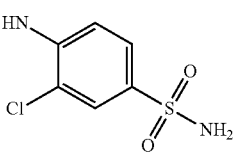 | 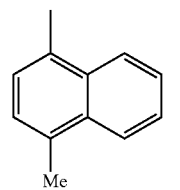 | H | A | A | A | A | A | C |
| 54 | CF$_2$H | 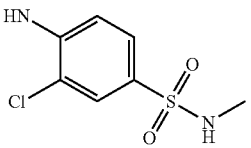 | | H | A | A | B | A | A | C |

TABLE 1-continued
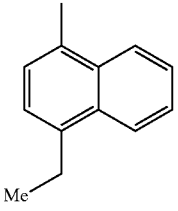
| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 55 | CFH₂ | 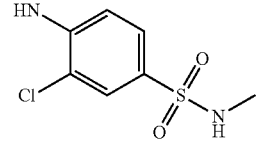 | 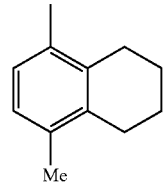 | H | A | A | B | B | A | C |
| 56 | CF₂H | 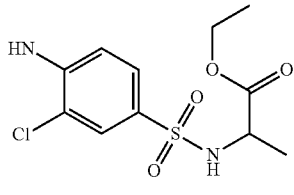 | 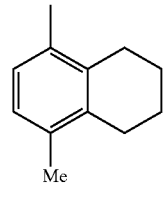 | H | A | A | C | A | C | C |
| 57 | CF₂H | 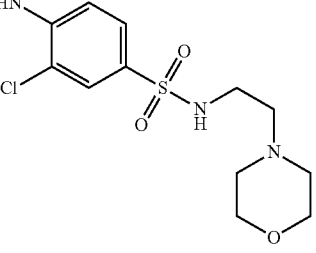 | 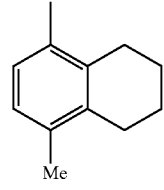 | H | A | A | B | A | B | C |
| 58 | CF₂H | 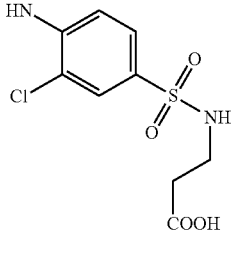 | 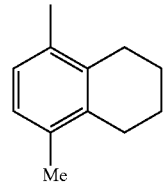 | H | B | C | C | A | C | C |
| 59 | CF₂H | 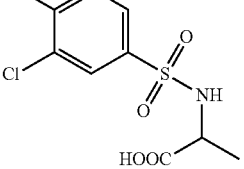 | 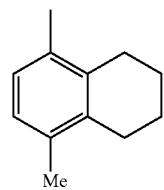 | H | C | C | C | A | C | C |
| 60 | CF₂H | 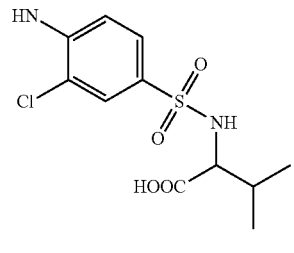 |  | H | C | C | C | A | C | C |

TABLE 1-continued

| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 61 | Br | 4-Me-1-F-naphthyl | 4-NH-3-Cl-benzenesulfonamide | H | A | A | A | A | A | C |
| 62 | Br | 4-Me-1-F-naphthyl | 4-NH-3-Me-benzenesulfonamide | H | A | A | C | A | C | C |
| 63 | CF₂H | 2,5,7-triMe-8-Me-quinolinyl | 4-NH-3-Cl-benzenesulfonamide | H | A | A | A | A | B | C |
| 64 | CF₂H | 2,5,7-triMe-8-Me-quinolinyl | 4-NH-3-Me-benzenesulfonamide | H | A | A | A | A | C | C |
| 65 | CFH₂ | 5,8-diMe-tetrahydronaphthyl | 4-NH-3-Me-benzenesulfonamide | H | A | A | B | A | C | C |
| 66 | H | 4-Me-1-cyclopropyl-naphthyl | 4-NH-3-Cl-benzenesulfonamide | H | A | A | C | A | B | C |

TABLE 1-continued

| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 67 | $CFH_2$ | 5,8-dimethyl-tetrahydronaphthalene with Et | 3-chloro-4-aminobenzenesulfonamide | H | A | A | A | A | A | C |
| 68 | $CF_2H$ | 4-methyl-1-cyclopentyl-naphthalene | 3-chloro-4-aminobenzenesulfonamide | H | A | A | C | A | A | C |
| 69 | $CF_2H$ | 4-methyl-1-cyclobutyl-naphthalene | 3-chloro-4-aminobenzenesulfonamide | H | A | A | A | A | A | B |
| 70 | I | 4-methyl-1-ethyl-naphthalene | 3-chloro-4-aminobenzenesulfonamide | H | A | A | A | A | B | C |
| 71 | $CF_2H$ | 4-methyl-1-isopropyl-naphthalene | 3-chloro-4-aminobenzenesulfonamide | H | A | A | A | A | A | C |
| 72 | Br | 8-methyl-6-methoxy-1-cyclopropyl-naphthalene | 3-chloro-4-aminobenzenesulfonamide | H | A | A | A | A | A | B |

TABLE 1-continued
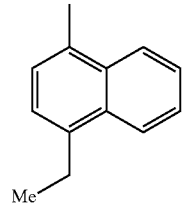
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 73 | Br | 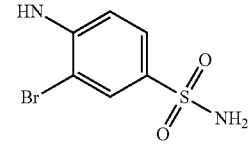 | 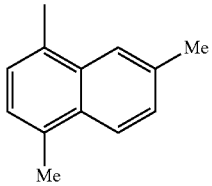 | H | A | A | A | A | A | B |
| 74 | Br | 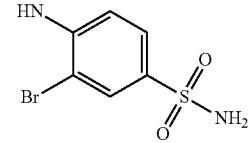 | 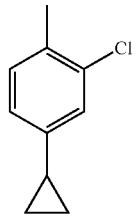 | H | A | A | A | A | A | B |
| 75 | Br | 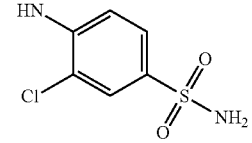 | 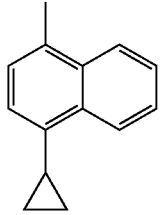 | H | A | A | A | A | A | C |
| 76 | Br | 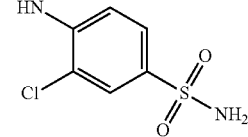 | 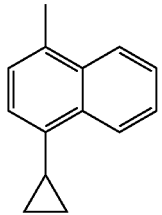 | Me | A | B | C | A | B | C |
| 77 | Br | 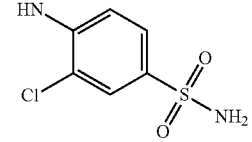 | 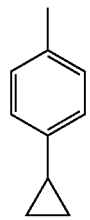 | H | A | B | C | A | B | C |
| 78 | Br | 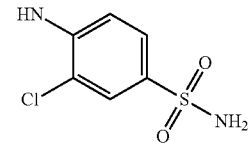 | | H | A | A | C | A | A | C |

TABLE 1-continued
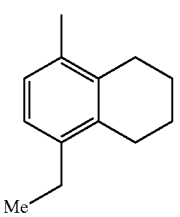
| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 79 | Br | 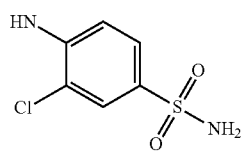 | 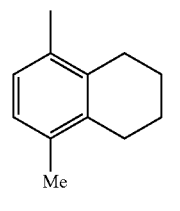 | H | A | A | A | A | A | B |
| 80 | Br | 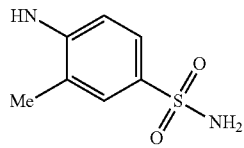 | 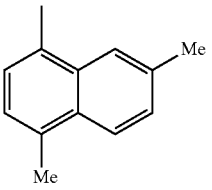 | H | A | A | A | A | A | B |
| 81 | Br | 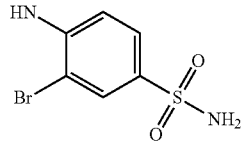 | 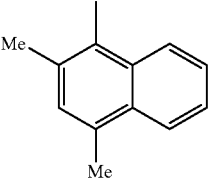 | H | A | A | A | A | A | B |
| 82 | CFH$_2$ | 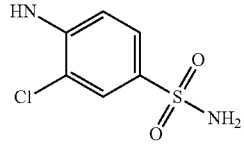 | 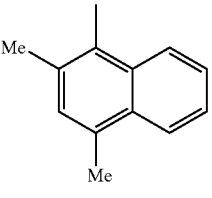 | H | A | A | A | A | B | C |
| 83 | CF$_3$ | 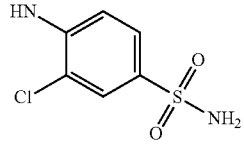 | 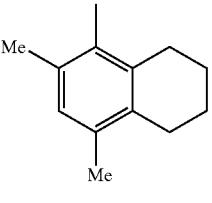 | H | A | A | A | A | C | C |
| 84 | CF$_3$ | 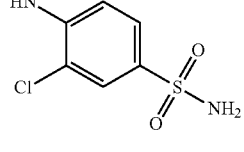 | 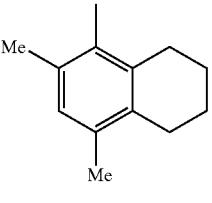 | H | A | A | A | A | A | C |

TABLE 1-continued

| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 85 | Br | 1-methyl-4-propyl-naphthyl | 3-chloro-4-amino-benzenesulfonamide | H | A | A | A | A | A | C |
| 86 | Br | 1-methyl-4-propyl-naphthyl | 3-methyl-4-amino-benzenesulfonamide | H | A | A | A | A | A | C |
| 87 | Br | 1-methyl-4-ethyl-naphthyl | 3-chloro-4-amino-benzenesulfonamide | H | A | A | A | A | A | B |
| 88 | Br | 3-methyl-4-methyl-phenyl-cyclopropyl | 3-chloro-4-amino-benzenesulfonamide | H | A | A | A | A | A | C |
| 89 | Cl | 1-methyl-4-cyclopropyl-naphthyl | 3-chloro-4-amino-benzenesulfonamide | H | A | A | A | A | A | C |
| 90 | Br | 3-trifluoromethoxy-4-methyl-phenyl-cyclopropyl | 3-chloro-4-amino-benzenesulfonamide | H | A | A | B | A | A | C |

TABLE 1-continued
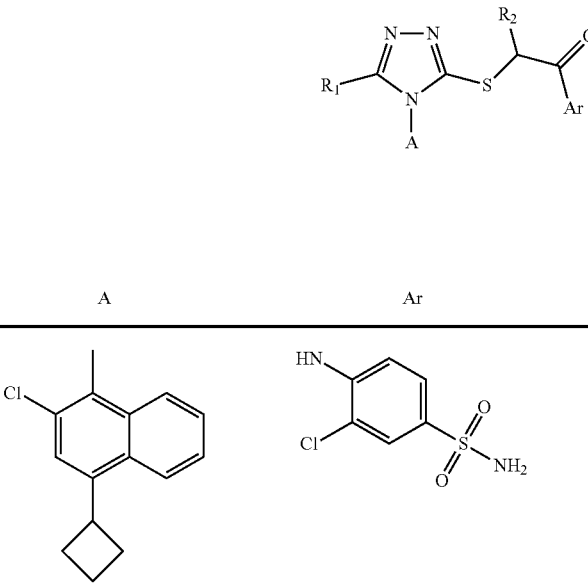
| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 91 | Br | 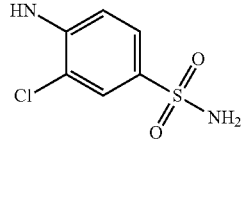 | 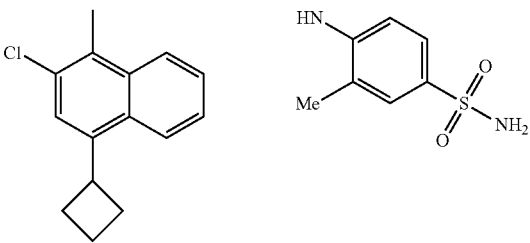 | H | A | A | A | A | A | B |
| 92 | Br | 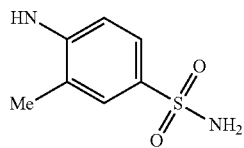 | 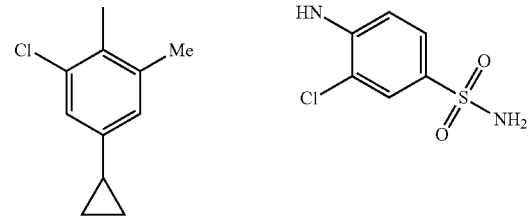 | H | A | A | A | A | A | B |
| 93 | Br | 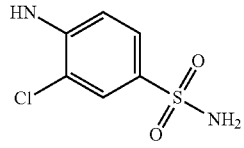 | 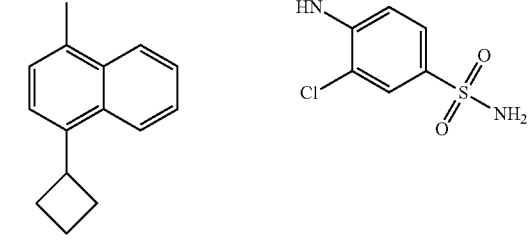 | H | A | A | A | A | A | C |
| 94 | Br | 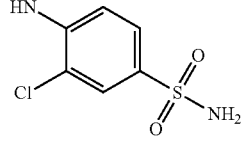 | 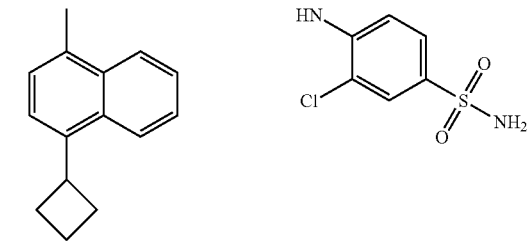 | H | A | A | A | A | A | C |
| 95 | Br | 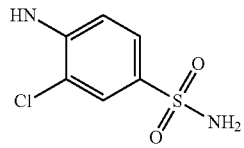 | | H | A | A | A | A | A | A |

TABLE 1-continued
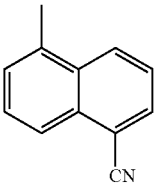
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 96 | CF₂H | 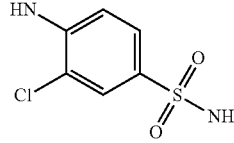 | 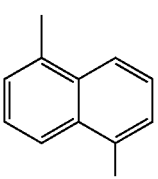 | H | A | A | C | B | C | C |
| 97 | CF₂H | 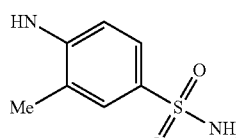 | 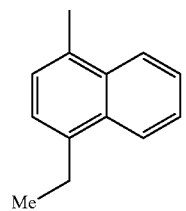 | H | ND | ND | ND | C | C | C |
| 98 | Br | 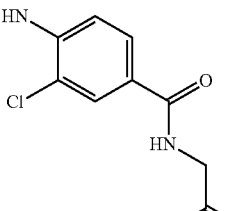 | 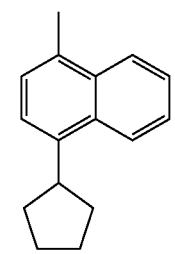 | H | A | A | A | A | A | B |
| 99 | CF₂H | 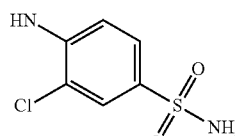 | 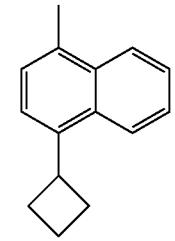 | H | A | A | C | A | A | C |
| 100 | CF₂H | 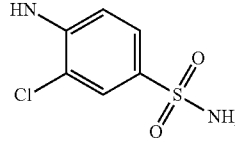 | 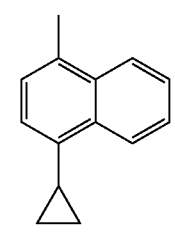 | H | A | A | A | A | B | B |
| 101 | Br | 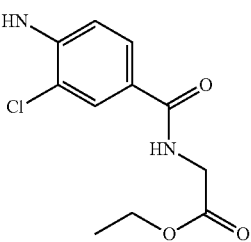 |  | H | A | A | A | A | B | A |

TABLE 1-continued
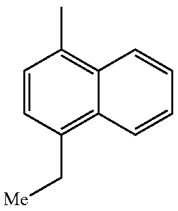
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 102 | Br | 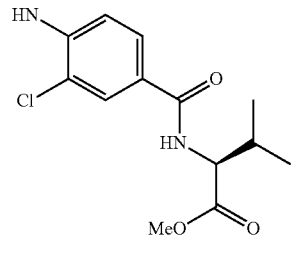 | 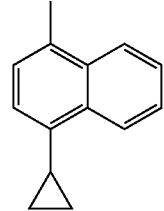 | H | A | A | A | B | A | A |
| 103 | Br | 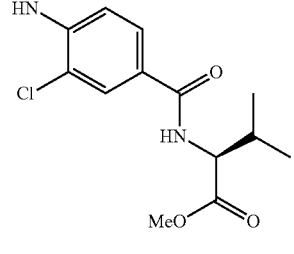 | 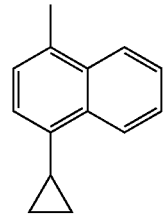 | H | A | A | B | A | A | B |
| 104 | Br | 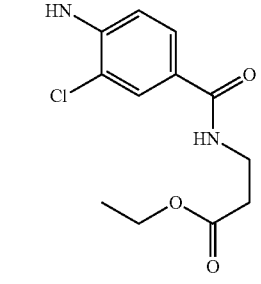 | 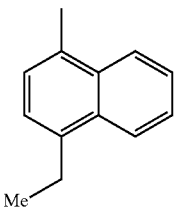 | H | A | A | A | A | A | A |
| 105 | Br | 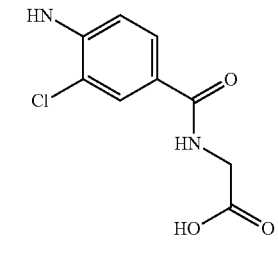 | 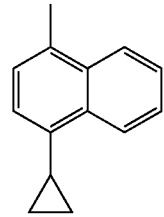 | H | A | A | B | A | A | C |
| 106 | Br | 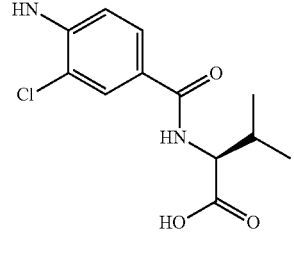 | | H | A | C | B | B | A | C |

TABLE 1-continued

| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 107 | Br | 4-Me, 1-Et-naphthyl | 3-Cl-4-NH-, N-(CH₂CO₂Et)benzamide | H | A | A | C | A | A | B |
| 108 | Br | 4-Me, 1-Et-naphthyl | 3-Cl-4-NH-, N-Me-N-(CH₂CO₂Et)benzamide | H | A | A | A | A | A | C |
| 109 | Br | 4-Me, 1-cPr-naphthyl | 3-Cl-4-NH-, N-Me-N-(CH₂CO₂Et)benzamide | H | A | A | A | B | A | C |
| 110 | Br | 4-Me, 1-cPr-naphthyl | 3-Cl-4-NH-, N-(CH₂CO₂H)benzamide | H | A | C | C | A | A | B |
| 111 | Br | 4-Me, 1-cPr-naphthyl | 3-Cl-4-NH-, N-Me-N-(CH₂CO₂H)benzamide | H | B | C | C | A | A | C |

TABLE 1-continued
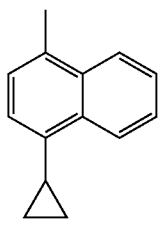
| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 112 | Br | 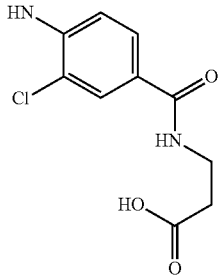 | 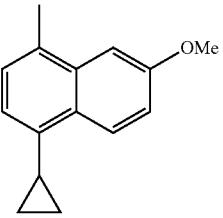 | H | A | C | C | A | A | C |
| 113 | Br | 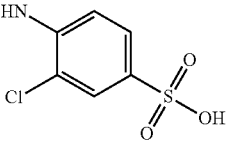 | 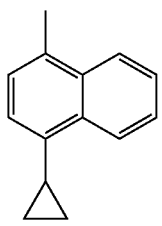 | H | B | B | C | A | A | B |
| 114 | Br | 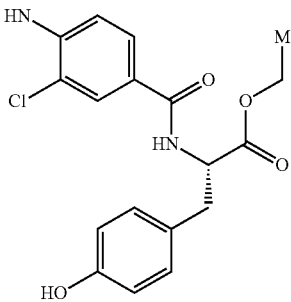 | 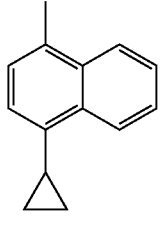 | H | A | A | C | B | A | B |
| 115 | Br | 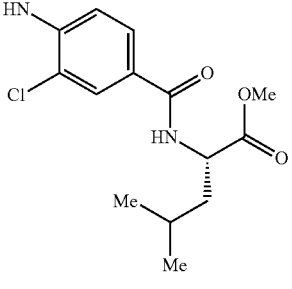 |  | H | A | A | B | A | A | B |

TABLE 1-continued

| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 116 | Br | 4-methyl-1-cyclopropylnaphthalenyl | 3-chloro-4-amino-N-(tyrosine)benzamide | H | B | C | C | A | A | B |
| 117 | Br | 4-methyl-1-cyclopropylnaphthalenyl | 3-chloro-4-amino-N-(leucine)benzamide | H | A | B | C | A | A | B |
| 118 | Br | 4-methyl-1-ethylnaphthalenyl | 3-chloro-4-amino-N-(2,2-dimethoxyethyl)benzamide | H | A | A | A | A | A | C |
| 119 | Br | 4-methyl-1-ethylnaphthalenyl | 3-chloro-4-amino-N-(2-(dimethylamino)ethyl)benzamide | H | A | A | A | A | A | C |
| 120 | Br | 4-methyl-1-ethylnaphthalenyl | 3-chloro-4-amino-N-(2,3-dihydroxypropyl)benzamide | H | A | A | A | A | A | C |

TABLE 1-continued
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 121 | Br | 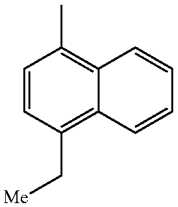 | 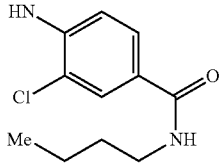 | H | A | A | A | B | A | C |
| 122 | Br | 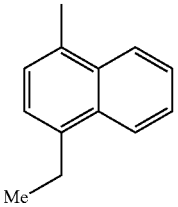 | 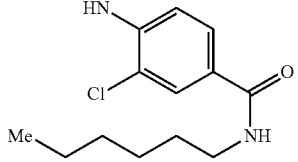 | H | A | A | B | A | A | C |
| 123 | Br | 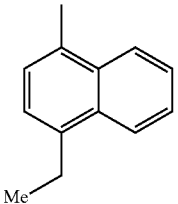 | 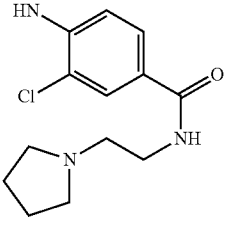 | H | A | A | A | A | A | C |
| 124 | Br | 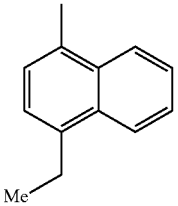 | 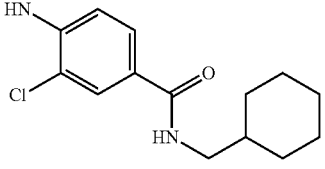 | H | A | A | A | A | A | C |
| 125 | Br | 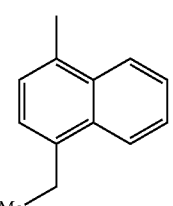 | 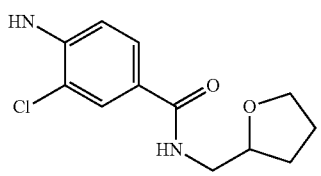 | H | A | A | A | A | B | A |
| 126 | Br | 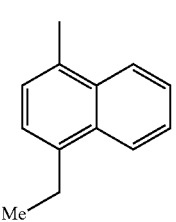 | 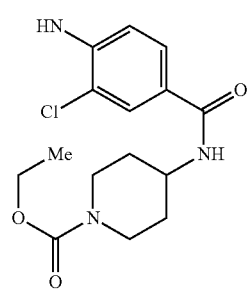 | H | A | A | A | A | A | C |

TABLE 1-continued
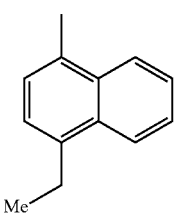
| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 127 | Br | 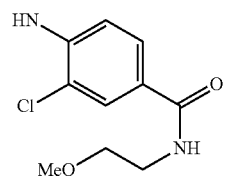 | 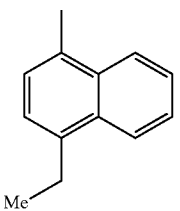 | H | A | A | A | A | A | A |
| 128 | Br | 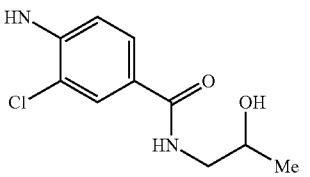 | 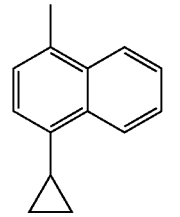 | H | A | A | A | A | A | B |
| 129 | Br | 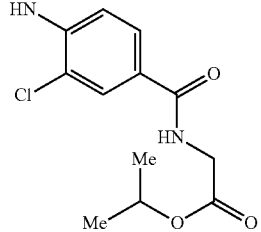 | 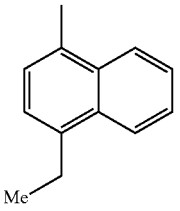 | H | A | A | A | A | A | A |
| 130 | Br | 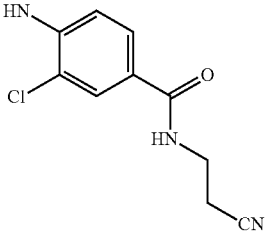 | 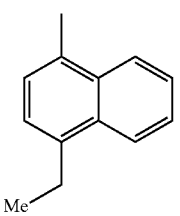 | H | A | A | A | A | B | B |
| 131 | Br | 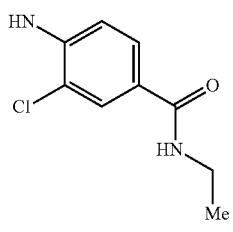 | | H | A | A | A | A | A | C |

TABLE 1-continued
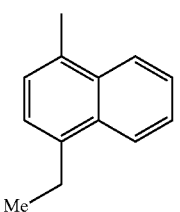
| No. | R¹ | A | Ar | R₂ | EC₅₀ WT (nM) | EC₅₀ Y181C (nM) | EC₅₀ Y188L (nM) | IC₅₀ WT RT (nM) | IC₅₀ Y181C (nM) | IC₅₀ Y188L (nM) |
|---|---|---|---|---|---|---|---|---|---|---|
| 132 | Br | 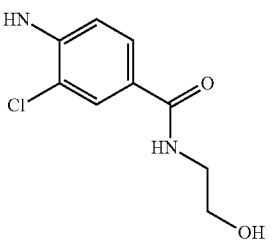 | 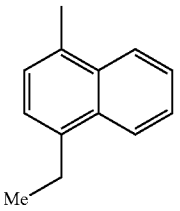 | H | A | A | A | A | A | B |
| 133 | Br | 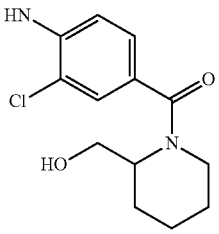 | 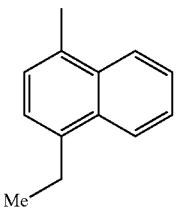 | H | A | A | A | A | A | C |
| 134 | Br | 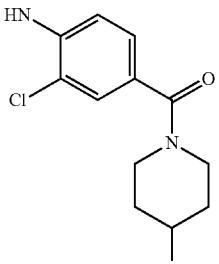 | 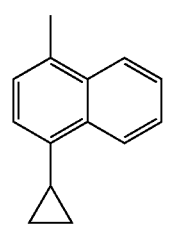 | H | A | A | A | A | A | C |
| 135 | Br | 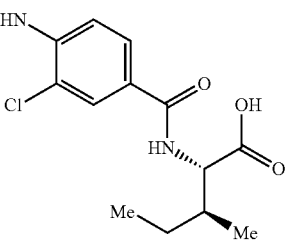 | 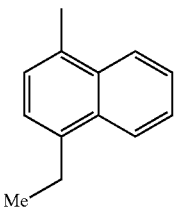 | H | A | A | C | A | B | B |
| 136 | Br | 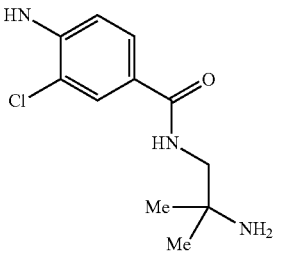 | | H | A | A | A | A | A | B |

TABLE 1-continued
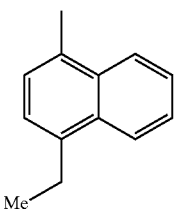
| No. | R¹ | A | Ar | R₂ | EC$_{50}$ WT (nM) | EC$_{50}$ Y181C (nM) | EC$_{50}$ Y188L (nM) | IC$_{50}$ WT RT (nM) | IC$_{50}$ Y181C (nM) | IC$_{50}$ Y188L (nM) |
|---|---|---|---|---|---|---|---|---|---|---|
| 137 | Br | 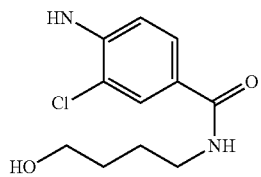 | 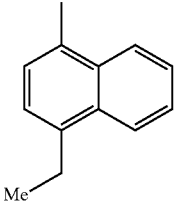 | H | A | A | A | A | A | A |
| 138 | Br | 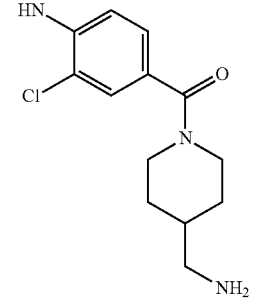 | 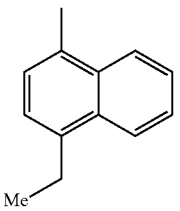 | H | A | A | A | A | A | C |
| 139 | Br | 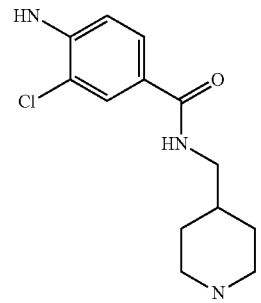 | 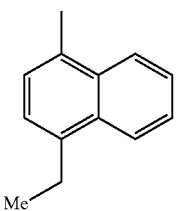 | H | A | A | B | C | C | C |
| 140 | Br | 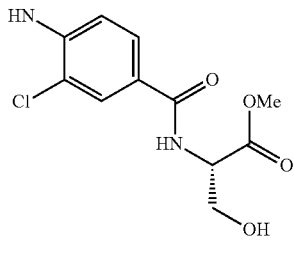 | 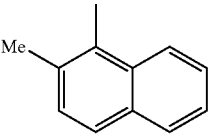 | H | A | A | A | A | A | A |
| 141 | Br | 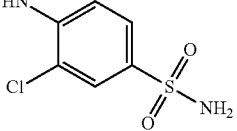 | | Me | A | | A | B | C | |

TABLE 1-continued

| No. | $R^1$ | A | Ar | $R_2$ | $EC_{50}$ WT (nM) | $EC_{50}$ Y181C (nM) | $EC_{50}$ Y188L (nM) | $IC_{50}$ WT RT (nM) | $IC_{50}$ Y181C (nM) | $IC_{50}$ Y188L (nM) |
|---|---|---|---|---|---|---|---|---|---|---|
| 142 | Br | 1-methyl-naphth-2-yl | 4-(HN)-3-Me-phenyl-SO₂NH₂ | Me | A | A | C | A | C | C |

We claim:

1. A compound of formula wherein:

P is selected from the group consisting of (a):

(a)

$R^1$ is selected from the group consisting of Cl, Br, I, $CF_3$, $CHF_2$; and $CH_2F$;

$R^2$ and $R^{2'}$ are independently selected from the group consisting of H, optionally substituted $C_{1-5}$acyl, 1-($C_{2-4}$acyloxy)$C_{1-4}$alkoxycarbonyl, and an acyl group derived from an α-amino acid;

$R^3$ is H or $CH_3$;

$R^0$ is selected from the group consisting of Cl, Br, $CF_3$ and methyl;

$R^P$ is $C_{3-6}$cycloalkyl; and $R^4$, $R^5$ and $R^6$ are independently selected from the group consisting of H, F, Br, $CH_3$, $CF_3$, $CFH_2$, $CF_2H$, isopropyl, cyclopropyl, $OCH_3$, OH, $OCF_3$, $NH_2$ and $NHCH_3$.

2. The compound of claim 1, wherein
P is a substituted naphthyl and
$R^1$ is selected from the group consisting of Br, $CF_3$, $CFH_2$, and $CF_2H$.

3. The compound of claim 2, wherein each of $R^4$, $R^5$, and $R^6$ is H.

4. The compound of claim 2, wherein $R^P$ is cyclopropyl.

5. The compound of claim 2, wherein
$R^1$ is Br and
$R^0$ is Cl.

6. A method for inhibiting an HIV reverse transcriptase, comprising contacting the HIV reverse transcriptase with a compound of formula wherein:

P is selected from the group consisting of (a):

(a)

$R^1$ is selected from the group consisting of Cl, Br, I, $CF_3$, $CHF_2$, and $CH_2F$;

$R^2$ and $R^{2'}$ are independently selected from the group consisting of H, optionally substituted $C_{1-5}$acyl, 1-($C_{2-4}$acyloxy)$C_{1-4}$alkoxycarbonyl, and an acyl group derived from an α-amino acid;

$R^3$ is H or $CH_3$;

$R^0$ is selected from the group consisting of Cl, Br, $CF_3$ and methyl;

$R^P$ is $C_{3-6}$cycloalkyl; and $R^4$, $R^5$ and $R^6$ are independently selected from the group consisting of H, F, Cl, Br, $CH_3$, $CF_3$, $CFH_2$, $CF_2H$, isopropyl, cyclopropyl, $OCH_3$, OH, $OCF_3$, $NH_2$ and $NHCH_3$.

7. The method of claim 6, wherein the HIV reverse transcriptase is a mutated reverse transcriptase.

8. The method of claim 7, wherein the mutated HIV reverse transcriptase is a K10Y, Y181C or Y188L mutant.

* * * * *